United States Patent [19]

Serban et al.

[11] 4,427,437
[45] Jan. 24, 1984

[54] USE OF 2-PHENOXYPYRIMIDINES AS HERBICIDES

[75] Inventors: Alexander Serban, Doncaster; Keith G. Watson, Box Hill; Richard B. Warner, Ringwood, all of Australia

[73] Assignee: ICI Australia Limited, Melbourne, Australia

[21] Appl. No.: 939,914

[22] Filed: Sep. 5, 1978

[30] Foreign Application Priority Data

Sep. 13, 1977 [AU] Australia ................................ 1626

[51] Int. Cl.³ .................... A01N 5/00; C07D 239/34
[52] U.S. Cl. ................................. 71/92; 74/76; 544/299; 544/301; 544/302; 544/303; 544/304; 544/305; 544/306; 544/309; 544/311; 544/312; 544/313; 544/314; 544/315; 544/316; 544/318
[58] Field of Search ................................. 71/76, 92

[56] References Cited

U.S. PATENT DOCUMENTS

| | | | |
|---|---|---|---|
| 3,126,271 | 3/1964 | Thompson et al. | 71/2.5 |
| 3,427,146 | 2/1969 | Tamura et al. | 71/76 |
| 3,897,440 | 7/1975 | Beck et al. | 71/92 |
| 3,947,437 | 3/1976 | Johnson | 71/92 |
| 3,969,101 | 7/1976 | Fischer | 71/76 |
| 3,974,276 | 8/1976 | Barlow et al. | 71/92 |

FOREIGN PATENT DOCUMENTS 109170 10/1974 Fed. Rep. of Germany .
42-9474 5/1967 Japan .

OTHER PUBLICATIONS

Jojima et al., "Agr. Biol. Chem.", vol. 30(9), 1966, pp. 896–905.

Primary Examiner—Donald G. Daus
Assistant Examiner—James H. Turnipseed
Attorney, Agent, or Firm—Cushman, Darby & Cushman

[57] ABSTRACT

A process of inhibiting the growth of, severely damaging, or killing plants which process comprises applying to the plant or to the growth medium thereof an effective amount of a composition comprising as active ingredient a compound of formula I:

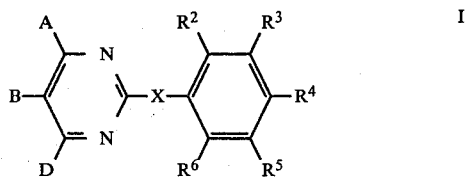

wherein A, B and D are independently chosen from the group consisting of hydrogen, halogen, hydroxy, nitro, cyano, thiocyano, optionally substituted alkyl, optionally substituted alkenyl, optionally substituted alkoxy, optionally substituted alkenyloxy, optionally substituted alkynyloxy, optionally substituted alkylthio, optionally substituted cycloalkyl, optionally substituted amino, optionally substituted phenyl, carboxy, alkoxycarbonyl, optionally substituted carbamoyl, sulfo, alkylsulfonyl and optionally substituted sulfamoyl; $R^2$, $R^3$, $R^4$, $R^5$ and $R^6$ are independently chosen from the group consisting of hydrogen, halogen, nitro, cyano, thiocyano, formyl, optionally substituted alkyl, optionally substituted alkenyl, optionally substituted cycloalkyl, optionally substituted alkylcarbonyl, optionally substituted amino, optionally substituted phenyl, optionally substituted carbamoyl, sulfo, alkoxysulfonyl, optionally substituted sulfamoyl and the groups $YR^1$ and

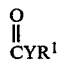

wherein Y is oxygen or sulphur and $R^1$ is chosen from the group consisting of hydrogen, optionally substituted alkyl, optionally substituted alkenyl, optionally substituted alkynyl, optionally substituted cycloalkyl, optionally substituted acyl, optionally substituted alkoxycarbonyl, optionally substituted phenyl and the cation of an inorganic or organic base; X is oxygen or sulphur; and B, $R^3$ and $R^5$ are not all hydrogen; or a geometrical or optical isomer thereof; or a tautomer thereof; or a salt thereof; and a carrier therefor.

24 Claims, No Drawings

USE OF 2-PHENOXYPYRIMIDINES AS HERBICIDES

This invention relates to processes for inhibiting the growth of, severely damaging, or killing plants by the use of certain pyrimidine derivatives; and to compositions for inhibiting the growth of, severely damaging, or killing plants; and to novel pyrimidine derivatives.

In their Japanese Patent No. 9474/67 (Application No. 12771/65) to Sankyo Co Ltd and their related paper in Agricultural and Biological Chemistry Vol. 30, No. 9, pp 896–905, 1966 Jojima and Tamura disclose that certain 2- and 4-phenoxypyrimidines show pre-emergent herbicidal activity against sensitive plant species such as radish and millet. However, the screen results reported by Jojima and Tamura were carried out under conditions where the test seeds were in direct contact with the chemical or a solution or suspension of the chemical under test and not under conditions more relevant to actual practice where the chemical under test is applied to the plant growth medium containing the seeds.

We have examined the herbicidal activity of preferred compounds specifically disclosed in the above cited Japanese Patent both by pre-emergence application of the chemical under test to the plant growth medium and by post-emergence application of the test chemical to the plant and plant growth medium but in our hands the chemicals showed little or no herbicidal activity when tested at technically acceptable rates on a wide range of plant species. However, we have now found that 2-phenoxypyrimidines not disclosed in the cited Japanese Patent which have a specific substitution pattern (i.e. those compounds in which the pyrimidyl ring is substituted in the 5-position and/or the phenyl ring is substituted in the 3- and/or 5-positions) not disclosed in the cited Japanese Patent have a high level of herbicidal activity when used at technically acceptable rates of application.

Accordingly we provide a process of inhibiting the growth of, severely damaging, or killing plants which process comprises applying to the plant or to the growth medium thereof an effective amount of a composition comprising as active ingredient a compound of formula I:

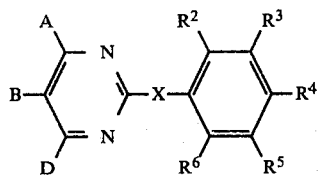

wherein A, B, and D are independently chosen from the group consisting of hydrogen, halogen, hydroxy, nitro, cyano, thiocyano, optionally substituted alkyl, optionally substituted alkenyl, optionally substituted alkoxy, optionally substituted alkenyloxy, optionally substituted alkynyloxy, optionally substituted alkylthio, optionally substituted cycloalkyl, optionally substituted amino, optionally substituted phenyl, carboxy, alkoxycarbonyl, optionally substituted carbamoyl, sulfo, alkylsulfonyl and optionally substituted sulfamoyl; $R^2$, $R^3$, $R^4$, $R^5$ and $R^6$ are independently chosen from the group consisting of hydrogen, halogen, nitro, cyano, thiocyano, formyl, optionally substituted alkyl, optionally substituted alkenyl, optionally substituted cycloalkyl, optionally substituted alkylcarbonyl, optionally substituted amino, optionally substituted phenyl, optionally substituted carbamoyl, sulfo, alkoxysulfonyl, optionally substituted sulfamoyl and the groups $YR^1$ and $$\underset{CYR}{\overset{O}{\|}}$$

wherein Y is oxygen or sulphur and $R^1$ is chosen from the group consisting of hydrogen, optionally substituted alkyl, optionally substituted alkenyl, optionally substituted alkynyl, optionally substituted cycloalkyl, optionally substituted acyl, optionally substituted alkoxycarbonyl, optionally substituted phenyl and the cation of an inorganic or organic base; X is oxygen or sulphur; and B, $R^3$ and $R^5$ are not all hydrogen; or a geometrical or optical isomer thereof; or a tautomer thereof; or a salt thereof; and a carrier therefor.

Suitable A, B and D include hydrogen, halogen, nitro, cyano, thiocyano, carboxy, and sulfo; $C_1$ to $C_6$ alkyl, $C_2$ to $C_6$ alkenyl, $C_1$ to $C_6$ alkoxy, $C_2$ to $C_6$ alkenyloxy, $C_2$ to $C_6$ alkynyloxy and $C_1$ to $C_6$ alkylthio wherein each group is optionally substituted with one or more substituents chosen from halogen, aryl, hydroxy, and $C_1$ to $C_6$ alkoxy; $C_3$ to $C_7$ cycloalkyl optionally substituted with one or more $C_1$ to $C_4$ alkyl groups; $NR^7R^8$ wherein $R^7$ and $R^8$ are independently chosen from hydrogen, $C_1$ to $C_6$ alkyl, $C_2$ to $C_6$ alkanoyl, aryl and aroyl; $NR^9R^{10}R^{11}]\oplus X\ominus$ wherein $X\ominus$ is an anion and $R^9$, $R^{10}$ and $R^{11}$ are chosen from $C_1$ to $C_6$ alkyl optionally substituted with one or more substituents chosen from halogen, aryl, hydroxy and $C_1$ to $C_6$ alkoxy, and phenyl optionally substituted with one or more substituents chosen from halogen, $C_1$ to $C_6$ alkyl, $C_1$ to $C_6$ alkoxy, nitro and cyano; $C_1$ to $C_6$-(alkoxy)carbonyl; $C_1$ to $C_6$-(alkyl)sulfonyl; carbamoyl and sulfamoyl optionally substituted on the amide nitrogen with one or two groups chosen from $C_1$ to $C_6$ alkyl and phenyl optionally substituted with one or more substituents chosen from halogen, $C_1$ to $C_6$ alkyl, $C_1$ to $C_6$ alkoxy, nitro and cyano; and phenyl optionally substituted with one or more substituents chosen from halogen, $C_1$ to $C_6$ alkyl, $C_1$ to $C_6$ alkoxy, nitro and cyano.

Suitable $R^2$, $R^3$, $R^4$, $R^5$ and $R^6$ include hydrogen, halogen, nitro, cyano, thiocyano, formyl and sulfo; $C_1$ to $C_6$ alkyl and $C_2$ to $C_6$ alkenyl wherein each group is optionally substituted with one or more substituents chosen from halogen, aryl, hydroxy and $C_1$ to $C_6$ alkoxy; $C_3$ to $C_7$ cycloalkyl optionally substituted with one or more $C_1$ to $C_4$ alkyl groups; $C_2$ to $C_6$ alkoxycarbonyl; $NR^7R^8$ and $NR^9R^{10}R^{11}]\oplus X\ominus$ wherein $R^7$, $R^8$, $R^9$, $R^{10}$, $R^{11}$ and $X\ominus$ are as hereinbefore defined; phenyl optionally substituted with one or more substituents chosen from halogen, $C_1$ to $C_6$ alkyl, $C_1$ to $C_6$ alkoxy, nitro and cyano; carbamoyl and sulfamoyl optionally substituted on the amide nitrogen with one or two groups chosen from $C_1$ to $C_6$ alkyl and phenyl optionally substituted with one or more substituents chosen from halogen, $C_1$ to $C_6$ alkyl, $C_1$ to $C_6$ alkoxy, nitro and cyano; $C_1$ to $C_6$-(alkoxy)sulfonyl; and the groups $YR^1$ and $$\underset{CYR^1}{\overset{O}{\|}}.$$

Suitable $R^1$ include hydrogen; $C_1$ to $C_{10}$ alkyl, $C_2$ to $C_{10}$ alkenyl and $C_2$ to $C_{10}$ alkynyl wherein each group is optionally substituted with one or more substituents chosen from halogen, aryl, hydroxy and $C_1$ to $C_6$ alkoxy; $C_3$ to $C_7$ cycloalkyl optionally substituted with one or more $C_1$ to $C_4$ alkyl groups; $C_1$ to $C_6$ alkanoyl; benzoyl optionally substituted on the phenyl ring with one or more substituents chosen from halogen, nitro, cyano, $C_1$ to $C_6$ alkyl and $C_1$ to $C_6$ alkoxy; phenyl optionally substituted with one or more substituents chosen from halogen, $C_1$ to $C_6$ alkyl, $C_1$ to $C_6$ alkoxy, nitro and cyano; the cation of an inorganic base such as, for example, an alkali metal ion or an alkaline earth metal ion; the cation of an organic base such as, for example, an ammonium ion $NR^{12}R^{13}R^{14}R^{15}]\oplus$ wherein $R^{12}$, $R^{13}$, $R^{14}$ and $R^{15}$ are independently chosen from the group hydrogen, $C_1$ to $C_6$ alkyl, $C_1$ to $C_6$ hydroxyalkyl, phenyl and benzyl; and the groups

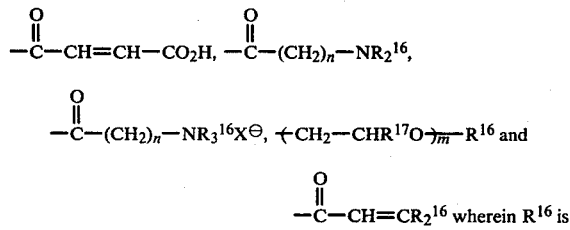

hydrogen or a $C_1$ to $C_6$ alkyl group, $R^{17}$ is hydrogen or methyl, n is an integer from 2 to 6, m is an integer from 2 to 20 and $X^\ominus$ is an anion.

Preferred values for A, B and D are hydrogen, halogen, cyano, $C_1$ to $C_6$ alkylthio, $C_1$ to $C_6$ alkylsulfonyl, $C_1$ to $C_6$-(alkoxy)carbonyl, $C_1$ to $C_6$ alkyl optionally substituted with halogen, $C_1$ to $C_6$ alkoxy optionally substituted with halogen, $C_2$ to $C_6$ alkenyl optionally substituted with halogen, $C_2$ to $C_6$ alkenyloxy optionally substituted with halogen, $C_2$ to $C_6$ alkynyloxy optionally substituted with halogen, $NR^7R^8$ wherein $R^7$ and $R^8$ are independently hydrogen or $C_1$ to $C_6$ alkyl, and phenyl optionally substituted with one or more substituents chosen from halogen, $C_1$ to $C_6$ alkyl, $C_1$ to $C_6$ alkoxy, nitro and cyano. Preferred X is oxygen.

Preferred values for $R^2$, $R^3$, $R^4$, $R^5$ and $R^6$ are hydrogen, halogen, nitro, cyano, formyl, $C_1$ to $C_6$-(alkyl)-carbonyl, methylenedioxy and ethylenedioxy wherein two adjacent carbon atoms of the phenyl ring are bridged, $NR^7R^8$ wherein $R^7$ and $R^8$ are independently hydrogen, $C_1$ to $C_6$ alkyl or $C_2$ to $C_6$ alkanoyl, $NR^9R^{10}R^{11}]\oplus X^\ominus$ wherein $R^9$, $R^{10}$ and $R^{11}$ are independently chosen from $C_1$ to $C_6$ alkyl and $X^\ominus$ is an anion, $C_1$ to $C_6$ alkyl and $C_2$ to $C_6$ alkenyl wherein each group is optionally substituted with one or more substituents chosen from halogen, hydroxy, $C_1$ to $C_6$ alkoxy and phenyl optionally substituted with one or more substituents chosen from halogen, $C_1$ to $C_6$ alkyl, $C_1$ to $C_6$ alkoxy, nitro and cyano, and the groups $YR^1$ and

$CYR^1$ wherein Y is oxygen and $R^1$ is chosen from the group consisting of hydrogen, $C_1$ to $C_6$ alkyl optionally substituted with halogen or $C_1$ to $C_6$ alkoxy, $C_2$ to $C_6$ alkenyl optionally substituted with halogen, $C_2$ to $C_6$ alkynyl, $C_1$ to $C_6$-(alkyl)carbonyl optionally substituted with halogen and the groups phenyl and benzyl wherein in each group the phenyl ring is optionally substituted with one or more substituents chosen from halogen, $C_1$ to $C_6$ alkyl, $C_1$ to $C_6$ alkoxy, nitro and cyano.

More preferred values for A, B and D are hydrogen, halogen, cyano, $C_1$ to $C_6$ alkylthio, $C_1$ to $C_6$ alkylsulfonyl, $C_1$ to $C_6$-(alkoxy)carbonyl $C_1$ to $C_6$ alkyl optionally substituted with halogen, $C_1$ to $C_6$ alkoxy, $NR^7R^8$ wherein $R^7$ and $R^8$ are independently hydrogen or $C_1$ to $C_6$ alkyl, and phenyl optionally substituted with one or more substituents chosen from halogen and nitro.

More preferred values for $R^2$, $R^3$, $R^4$, $R^5$ and $R^6$ are hydrogen, hydroxy, halogen, nitro, cyano, formyl, $C_1$ to $C_6$-(alkyl)carbonyl; methylenedioxy wherein two adjacent carbon atoms of the phenyl ring are bridged, $NR^7R^8$ wherein $R^7$ and $R^8$ are independently hydrogen, $C_1$ to $C_6$ alkyl or $C_2$ to $C_6$ alkanoyl, $NR^9R^{10}R^{11}]\oplus X^\ominus$ wherein $R^9$, $R^{10}$ and $R^{11}$ are independently chosen from $C_1$ to $C_6$ alkyl and $X^\ominus$ is an anion, $C_1$ to $C_6$ alkyl optionally substituted with halogen, $C_2$ to $C_6$ alkenyl optionally substituted with halogen, benzyl optionally substituted in the aromatic ring with halogen, $C_1$ to $C_6$ alkoxy optionally substituted with halogen, $C_2$ to $C_6$ alkenyloxy optionally substituted with halogen, $C_2$ to $C_6$ alkynyloxy, $C_2$ to $C_6$ alkanoyloxy optionally substituted with halogen, $C_1$ to $C_6$-(alkoxy)-carbonyl and the groups phenoxy, benzyloxy and benzoyloxy in which in each group the aromatic ring is optionally substituted with one or more substituents chosen from halogen, $C_1$ to $C_6$ alkyl, $C_1$ to $C_6$ alkoxy, nitro and cyano.

As a general rule we have found that the compounds more efficacious in the process of the invention are those compounds of formula I in which the pyrimidyl ring is substituted in the 5-position and the phenyl ring is substituted in the 3- and/or 5-positions.

Accordingly in a further embodiment the invention provides a process as described above wherein in the compound of formula I:

X is oxygen;

A, B, D are independently chosen from the group consisting of hydrogen, fluorine, chlorine, bromine, iodine, $C_1$ to $C_6$ alkyl optionally substituted with one or more halogens chosen from fluorine and chlorine, and $C_1$ to $C_6$-(alkoxy)-carbonyl;

$R^2$, $R^3$, $R^4$, $R^5$ and $R^6$ are independently chosen from hydrogen, fluorine, chlorine, bromine, iodine, nitro, cyano, $C_1$ to $C_6$ alkyl optionally substituted with one or more halogens chosen from fluorine, chlorine and bromine, $C_1$ to $C_6$ alkoxy optionally substituted with one or more halogens, chosen from fluorine and chlorine, $C_2$ to $C_6$ alkenyloxy optionally substituted with one or more halogens chosen from fluorine and chlorine, $C_2$ to $C_6$ alkynyloxy, and the groups benzyl, benzyloxy and phenoxy each optionally substituted in the aromatic ring with halogen;

B is a substituent other than hydrogen; and at least one of $R^3$ and $R^5$ is a substituent other than hydrogen.

Compounds even more preferred for use in the process of the invention are those compounds of formula I which are unsubstituted in the 4- and 6-positions of the pyrimidine ring.

Thus in an even more preferred embodiment the invention provides a process as described above wherein in the compound of formula I:

X is oxygen;

A and D are both hydrogen;

B is selected from the group consisting of fluorine, chlorine, bromine, iodine, methyl and ethyl;

$R^2$, $R^3$, $R^4$, $R^5$ and $R^6$ are independently chosen from the group consisting of hydrogen, fluorine, chlorine, bromine, iodine, $C_1$ to $C_6$ alkyl optionally substituted with one or more halogens chosen from fluorine and chlorine, $C_1$ to $C_6$ alkoxy optionally substituted with one or more halogens chosen from fluorine and chlorine, $C_2$ to $C_6$ alkenyloxy optionally substituted with one or more halogens chosen from fluorine and chlorine, $C_2$ to $C_6$ alkynyloxy and the groups benzyl, benzyloxy and phenoxy each optionally substituted in the aromatic ring with one or more halogen atoms chosen from fluorine and chlorine; and wherein at least one of $R^3$ and $R^5$ is not hydrogen.

Particular examples of compounds of formula I include:

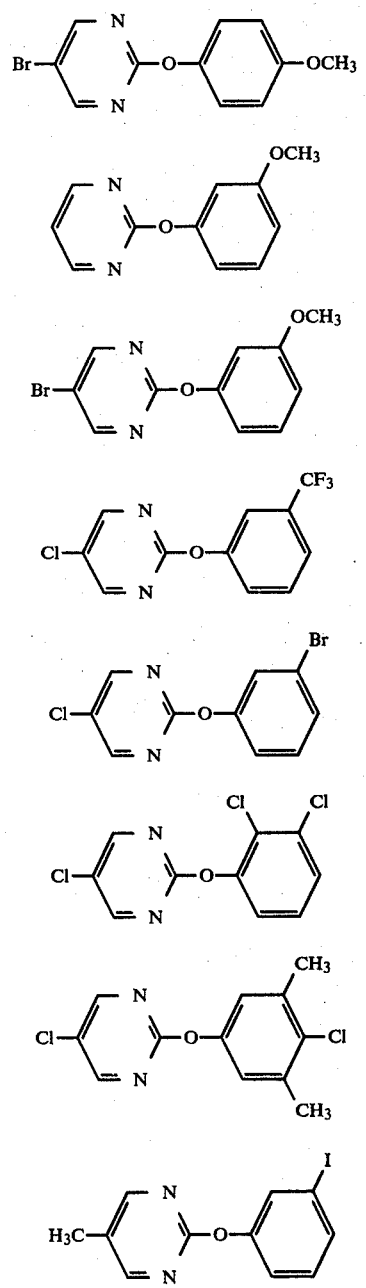

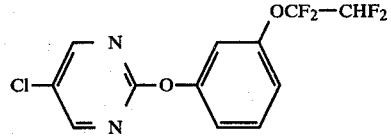

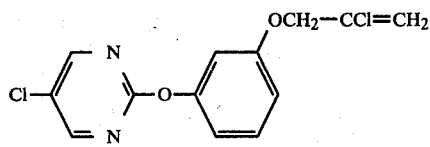

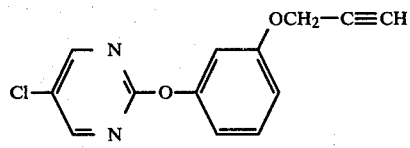

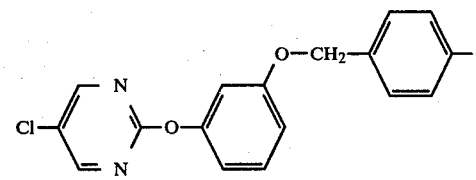

Those compounds or use in the method of the invention which have a basic functional group may be applied in the form of an acid addition salt. Suitable acid addition salts may be prepared from organic or inorganic mineral acids such as, for example, hydrochloric acid, hydrobromic acid, sulphuric acid, phosphoric acid, maleic acid, acetic acid, nitric acid, benzoic acid, citric acid, succinic acid, malic acid and the like.

Those compounds of use in the method of the invention which have an acidic functional group may be applied in the form of a base addition salt. Suitable base addition salts may be prepared from organic and inorganic bases such as, for example, mono-, di- and triethanolamines and the alkali metal and alkaline earth metal hydroxides and carbonates.

As hereinbefore described we have found that the compounds more efficacious in the process of the invention are those compounds in which the pyrimidyl ring is substituted in the 5-position and/or the phenyl ring is substituted in the 3- and/or 5-positions. Compounds of formula I having these substitution patterns are believed to be novel compounds and therefore in a further embodiment the invention provides:

(a) a compound of formula I wherein A, D, $R^2$, $R^3$, $R^4$, $R^5$ and $R^6$ may take any of the values hereinbefore defined, X is oxygen and B is chosen from halogen, cyano, $C_1$ to $C_6$ alkylthio, $C_1$ to $C_6$ alkylsulfonyl, $C_1$ to $C_6$-(alkoxy)carbonyl, $C_1$ to $C_6$ alkyl optionally substituted with halogen, $C_1$ to $C_6$ alkoxy, $NR^7R^8$ wherein $R^7$ and $R^8$ are independently hydrogen or $C_1$ to $C_6$ alkyl, and phenyl optionally substituted with one or more substituents chosen from halogen and nitro;

(b) a compound of formula I wherein A, B, D, $R^2$, $R^3$, $R^4$, $R^5$ and $R^6$ may take any of the values hereinbefore defined, X is oxygen, and at least one of $R^3$ and $R^5$ is chosen from the group consisting of hydroxy, halogen, nitro, cyano, formyl, $C_1$ to $C_6$-(alkyl)-carbonyl, methylenedioxy wherein two adjacent carbon atoms of the phenyl ring are bridged, $NR^7R^8$ wherein $R^7$ and $R^8$ are independently hydrogen, $C_1$ to $C_6$ alkyl or $C_2$ to $C_6$ alkanoyl, $NR^9R^{10}R^{11}]\oplus X^\ominus$ wherein $R^9$, $R^{10}$, and $R^{11}$ are independently chosen from $C_1$ to $C_6$ alkyl and $X^\ominus$ is an anion, $C_1$ to $C_6$ haloalkyl; $C_2$ to $C_6$ alkenyl optionally substituted with halogen, benzyl optionally substituted in the aromatic ring with halogen, $C_1$ to $C_6$ alkoxy optionally substituted with halogen, $C_2$ to $C_6$ alkenyloxy optionally substituted with halogen, $C_2$ to $C_6$ alkynyloxy, $C_2$ to $C_6$ alkanoyloxy optionally substituted with halogen, $C_1$ to $C_6$-(alkoxy)carbonyl and the groups phenoxy, benzyloxy and benzoyloxy in which in each group the aromatic ring is optionally substituted with one or more substituents chosen from halogen, $C_1$ to $C_6$ alkyl, $C_1$ to $C_6$ alkoxy, nitro and cyano; and (c) a compound of formula I wherein X is oxygen and A, B, D, $R^2$, $R^3$, $R^4$, $R^5$ and $R^6$ may take any of the values hereinbefore defined provided that B is a substituent other than hydrogen and at least one of $R^3$ and $R^5$ is a substituent other than hydrogen.

Certain of the novel compounds in which at least one of $R^2$, $R^3$, $R^4$, $R^5$ and $R^6$ is a hydroxy group are useful intermediates in the preparation of other compounds of the invention and in the preparation of other pyrimidine herbicides.

Thus the invention provides in yet a further embodiment a novel compound of formula I as hereinbefore defined wherein at least one of $R^2$, $R^3$, $R^4$, $R^5$ and $R^6$ is a hydroxy group.

The invention includes all of the novel specific compounds detailed in Table I below.

TABLE I

| Compound No | A | B | D | X | $R^2$ | $R^3$ | $R^4$ | $R^5$ | $R^6$ |
|---|---|---|---|---|---|---|---|---|---|
| 1 | H | Br | H | O | H | H | $CH_3O$ | H | H |
| 2 | H | Cl | H | O | H | H | $CH_3O$ | H | H |
| 3 | H | Cl | H | O | H | $CH_3O$ | H | H | H |
| 4 | H | H | H | O | H | $CH_3O$ | H | H | H |
| 5 | H | H | H | O | H | Cl | H | H | H |
| 6 | H | I | H | O | H | $CH_3O$ | H | H | H |
| 7 | H | Br | H | O | H | $CH_3O$ | H | H | H |
| 8 | H | Cl | H | O | H | Cl | H | H | H |
| 9 | $CH_3$ | Br | $CH_3$ | O | H | Cl | H | H | H |
| 10 | $CH_3$ | H | $CH_3$ | O | H | Cl | H | H | H |
| 11 | H | Cl | H | O | Cl | H | H | H | H |
| 12 | H | Cl | H | O | $CH_3O$ | H | H | H | H |
| 13 | H | Cl | H | O | H | Cl | H | Cl | H |
| 14 | H | Cl | H | O | H | $CF_3$ | H | H | H |
| 15 | H | Br | H | O | H | Cl | H | H | H |
| 16 | H | H | H | S | H | Cl | H | H | H |
| 17 | $CH_3$ | Br | H | O | H | Cl | H | H | H |
| 18 | H | $C_6H_5$ | H | O | H | Cl | H | H | H |
| 19 | H | Cl | H | O | H | $C_3H_7O$ | H | H | H |
| 20 | H | Cl | H | O | Cl | Cl | H | H | H |
| 21 | H | Cl | H | O | H | F | H | H | H |
| 22 | H | Cl | H | O | H | Br | H | H | H |
| 23 | H | Cl | H | O | H | Cl | Cl | H | H |
| 24 | H | CN | H | O | H | Cl | H | H | H |
| 25 | H | Cl | H | O | H | H | H | H | H |
| 26 | H | Cl | H | O | H | H | Cl | H | H |
| 27 | H | Cl | H | O | H | H | $CF_3$ | H | H |
| 28 | $NMe_2$ | H | H | O | H | Cl | H | H | H |
| 29 | H | Cl | H | O | Cl | H | H | H | Cl |
| 30 | H | $CO_2Et$ | H | O | H | Cl | H | H | H |
| 31 | H | Cl | H | O | Cl | H | Cl | H | H |
| 32 | H | Cl | H | O | Cl | H | H | Cl | H |
| 33 | H | Cl | H | O | H | $CH_3$ | H | H | H |
| 34 | $NMe_3$ | Br | H | O | H | Cl | H | H | H |
| 35 | H | Br | H | O | H | $CF_3$ | H | H | H |
| 36 | $CH_3$ | H | $CH_3$ | O | H | $CF_3$ | H | H | H |
| 37 | H | Cl | H | O | H | $CF_3$ | $NO_2$ | H | H |
| 38 | H | $CH_3$ | H | O | H | $CF_3$ | H | H | H |
| 39 | H | Cl | H | O | H | OEt | H | H | H |
| 40 | H | Cl | H | O | H | $CH_3CONH$ | H | H | H |
| 41 | H | Cl | H | O | $CH_3$ | $CH_3$ | Cl | H | H |
| 42 | H | Cl | H | O | H | $CO_2Et$ | H | H | H |
| 43 | H | Cl | H | O | H | CN | H | H | H |
| 44 | H | Cl | H | O | H | $NO_2$ | H | H | H |
| 45 | H | Cl | H | O | H | CHO | H | H | H |
| 46 | H | Cl | H | O | $CH_3$ | $CH_3$ | H | H | H |
| 47 | H | Cl | H | O | H | $CH_3$ | Cl | $CH_3$ | H |
| 48 | H | Cl | H | O | Br | H | $CH_3$ | H | Br |
| 49 | H | Cl | H | O | H | $NMe_2$ | H | H | H |
| 50 | H | Cl | H | O | Cl | H | H | $CH_3O$ | H |
| 51 | H | Br | H | O | Cl | H | $CH_3O$ | H | H |
| 52 | H | Cl | H | O | $CH_3O$ | $CH_3O$ | H | H | H |
| 53 | H | Cl | H | O | H | $O-CH_2-O$ | | H | H |
| 54 | H | F | H | O | H | $CF_3$ | H | H | H |
| 55 | H | Cl | H | O | H | $C_2H_5$ | H | H | H |
| 56 | H | Cl | H | O | H | a | H | H | H |
| 57 | $CH_3O$ | Br | H | O | H | $CF_3$ | H | H | H |

TABLE I-continued

| Compound No | A | B | D | X | R² | R³ | R⁴ | R⁵ | R⁶ |
|---|---|---|---|---|---|---|---|---|---|
| 58 | H | Cl | H | O | H | Br | H | CH₃ | H |
| 59 | H | Br | H | O | H | Br | H | CH₃ | H |
| 60 | H | Cl | H | S | H | Cl | H | H | H |
| 61 | H | Cl | H | S | H | CH₃O | H | H | H |
| 62 | H | Cl | H | S | H | CF₃ | H | H | H |
| 63 | H | Cl | H | O | H | Cl | CH₃O | H | H |
| 64 | H | Br | H | O | Cl | Cl | H | H | H |
| 65 | H | Br | H | O | H | CH₃ | Cl | H | H |
| 66 | H | Br | H | O | Cl | H | H | H | Cl |
| 67 | H | Cl | H | O | H | CH₃ | Cl | H | H |
| 68 | H | Cl | H | O | H | b | H | H | H |
| 69 | H | Cl | H | O | H | x | H | H | H |
| 70 | CO₂Et | CH₃ | H | O | H | Br | H | H | H |
| 71 | H | Cl | H | O | H | Br | H | H | H |
| 72 | H | Cl | H | O | H | c | H | H | H |
| 73 | H | H | H | O | H | Br | H | H | H |
| 74 | H | CH₃ | H | O | H | CH₃O | H | H | H |
| 75 | H | CH₃ | H | O | Cl | Cl | H | H | H |
| 76 | H | H | H | O | H | CF₃ | H | H | H |
| 77 | H | CH₃ | H | O | H | CH₃ | H | H | H |
| 78 | H | I | H | O | H | CF₃ | H | H | H |
| 79 | H | Cl | H | O | H | d | H | H | H |
| 80 | H | Br | H | O | H | H | CF₃ | H | H |
| 81 | H | Cl | H | O | H | ⊕NMe₃I⊖ | H | H | H |
| 82 | H | Br | H | O | H | CH₃ | H | H | H |
| 83 | H | Cl | H | O | H | CH₃CO₂ | H | H | H |
| 84 | H | Br | H | O | H | CH₃ | Cl | C₂H₅ | H |
| 85 | H | e | H | O | H | CF₃ | H | H | H |
| 86 | H | f | H | O | H | CF₃ | H | H | H |
| 87 | H | Cl | H | O | H | g | H | H | H |
| 88 | H | Cl | H | O | H | h | H | H | H |
| 89 | H | Cl | H | O | H | ClCH₂CO₂ | H | H | H |
| 90 | H | Cl | H | O | H | j | H | H | H |
| 91 | H | Cl | H | O | H | C₂H₅O | NO₂ | H | H |
| 92 | H | Cl | H | S | H | H | CH₃O | H | H |
| 93 | CH₃S | Cl | H | O | H | Br | H | H | H |
| 94 | CH₃NH | Cl | H | O | H | Br | H | H | H |
| 95 | CH₃NH | Cl | H | O | H | CF₃ | H | H | H |
| 96 | H | Cl | H | O | H | CH₃ | Br | CH₃ | H |
| 97 | H | Cl | H | O | Cl | H | CH₃O | H | H |
| 98 | H | Cl | H | O | CH₃O | H | C₂H₅ | H | H |
| 99 | H | Cl | H | O | CH₃O | H | Cl | H | H |
| 100 | H | Cl | H | O | CH₃O | H | k | H | H |
| 101 | H | I | H | O | H | CF₃ | H | H | H |
| 102 | H | Cl | H | O | H | CO₂Et | NO₂ | H | H |
| 103 | Cl | H | H | O | H | CF₃ | H | H | H |
| 104 | H | Cl | H | O | CH₃ | CH₃ | Cl | CH₃ | H |
| 105 | H | C₂H₅O | H | O | H | CF₃ | H | H | H |
| 106 | H | Cl | H | O | H | CH₃ | Cl | C₂H₅ | H |
| 107 | H | CF₃ | H | O | H | CH₃ | Cl | CH₃ | H |
| 108 | H | Cl | H | O | H | l | H | H | H |
| 109 | H | Cl | H | O | H | m | H | H | H |
| 110 | H | Cl | H | O | H | n | H | H | H |
| 111 | H | Cl | H | O | H | Cl | H | CH₃O | H |
| 112 | H | Cl | H | O | H | CF₃ | Cl | H | H |
| 113 | CH₃S | Cl | H | O | H | CF₃ | H | H | H |
| 114 | H | Cl | H | O | H | o | H | H | H |
| 115 | H | CH₃SO₂ | H | O | H | CF₃ | H | H | H |
| 116 | H | Cl | H | O | H | p | H | H | H |
| 117 | H | Cl | H | O | H | q | H | H | H |
| 118 | H | Cl | H | O | H | CH₃ | CH₃ | CH₃ | H |
| 119 | H | Cl | H | O | H | CH₃ | H | CH₃ | H |
| 120 | H | Cl | H | O | H | I | H | H | H |
| 121 | H | Cl | H | O | H | r | H | H | H |
| 122 | H | NMe₂ | H | O | H | Br | H | H | H |
| 123 | H | CH₃ | H | O | H | CH₃ | Cl | CH₃ | H |
| 124 | CCl₃ | H | O | H | Br | H | H | H | |
| 125 | H | Cl | H | O | H | CH₃O | H | CH₃O | H |
| 126 | H | Cl | H | O | H | s | H | H | H |
| 127 | H | Cl | H | O | H | CH₃ | H | x | H |
| 128 | H | Cl | H | O | Cl | H | Cl | H | Cl |
| 129 | H | Cl | H | O | Cl | Cl | Cl | H | H |
| 130 | H | C₂H₅ | H | O | H | Br | H | H | H |
| 131 | H | CH₃ | H | O | H | q | H | H | H |
| 132 | H | Cl | H | O | H | Cl | H | d | H |

TABLE I-continued

| Compound No | A | B | D | X | R² | R³ | R⁴ | R⁵ | R⁶ |
|---|---|---|---|---|---|---|---|---|---|
| 133 | H | CCl₃ | H | O | H | CF₃ | H | H | H |
| 134 | H | Br | H | S | H | H | CH₃O | H | H |
| 135 | H | Cl | H | O | CF₃ | H | H | H | H |
| 136 | H | Cl | H | O | H | j | H | H | H |
| 137 | H | Cl | H | O | H | CH₃CO | H | H | H |
| 138 | CO₂Et | Cl | H | O | H | CF₃ | H | H | H |
| 139 | CF₂Cl | H | H | O | H | Br | H | H | H |
| 140 | H | Cl | H | O | H | Cl | H | y | H |
| 141 | H | Cl | H | O | H | t | H | H | H |
| 142 | H | Cl | H | O | j | H | H | H | H |
| 143 | CCl₃ | H | H | O | H | q | H | H | H |
| 144 | H | Cl | H | O | z | H | H | H | H |
| 145 | H | CH₃ | H | O | H | I | H | H | H |
| 146 | H | Br | H | O | H | I | H | H | H |
| 147 | H | Br | H | O | H | q | H | H | H |
| 148 | H | Cl | H | O | H | Cl | H | j | H |
| 149 | H | C₂H₅ | H | O | H | I | H | H | H |
| 150 | H | C₂H₅ | H | O | H | q | H | H | H |
| 151 | H | Cl | H | O | u | H | H | H | H |
| 152 | H | Br | H | O | H | Br | H | H | H |
| 153 | CCl₃ | H | H | O | H | I | H | H | H |
| 154 | H | Cl | H | O | H | Cl | Cl | Cl | H |
| 155 | H | C₂H₅O | H | O | H | q | H | H | H |
| 156 | H | Cl | H | O | H | v | H | H | H |
| 157 | CCl₃ | H | CCl₃ | O | H | Br | H | H | H |
| 158 | H | Cl | H | O | w | H | H | H | H |
| 159 | H | Cl | H | O | H | u | H | H | H |
| 160 | H | Cl | H | O | H | Cl | CH₃O | Cl | H |
| 161 | H | Cl | H | O | H | w | H | H | H |
| 162 | H | I | H | O | H | H | OH | H | H |
| 163 | H | Cl | H | O | H | OH | NO₂ | H | H |
| 164 | H | Cl | H | O | H | NO₂ | OH | H | H |
| 165 | H | Cl | H | S | H | H | OH | H | H |
| 166 | H | Cl | H | O | H | CF₃ | OH | H | H |
| 167 | H | Cl | H | O | OH | H | H | H | H |
| 168 | H | Cl | H | O | H | OH | H | H | H |
| 169 | H | Br | H | O | Cl | H | OH | H | H |
| 170 | H | Br | H | S | H | H | OH | H | H |
| 171 | H | Br | H | O | H | H | OH | H | H |
| 172 | H | Br | H | O | H | NO₂ | OH | NO₂ | OH |
| 173 | H | Cl | H | O | H | H | OH | H | H |
| 174 | H | Cl | H | O | Cl | H | OH | H | H |
| 175 | H | Cl | H | O | OH | H | C₂H₅ | H | H |
| 176 | H | Cl | H | O | OH | H | Cl | H | H |
| 177 | H | Cl | H | O | H | OH | H | Cl | H | a C₆H₅CO₂
b (CH₃)₃C
c CH₂=CH—CH₂—O
d CH≡C—CH₂—O
e 4-ClC₆H₄
f 4-NO₂C₆H₄
g CH₂=CCl—CH₂—O
h ClCH₂—CH₂—CH₂—O
j 4-ClC₆H₄CH₂O
k CH₂=CH—CH₂
l C₆H₅CH₂O
m 2-ClC₆H₄CH₂O
n 2,4-Cl₂C₆H₃CH₂O
o 4-NO₂C₆H₄CH₂O
p 4-FC₆H₄CH₂O
q F₂CH—CF₂—O
r 3-ClC₆H₄CH₂O
s 4-CH₃OC₆H₄CH₂O
t 3,4-Cl₂C₆H₃CH₂O
u 4-ClC₆H₄O
v Br₂C=CH
w 4-FC₆H₄O
x (CH₃)₂CH
y (CH₃)₂CHO
z C₆H₅CH₂

The novel compounds of the invention may be prepared by methods known in the art for the preparation of analogous compounds. Thus, in yet a further aspect, the invention provides processes for the preparation of the novel compounds of formula I.

Compounds of formula I wherein A, B, D, R², R³, R⁴, R⁵, R⁶ and X are as hereinbefore defined may be prepared by the condensation of the appropriate pyrimidine of formula II, wherein L is a good leaving group (for example alkylsulfonyl, chlorine, bromine or iodine) with the appropriate phenol or thiophenol of formula III, preferably in the presence of an alkaline material, according to SCHEME A.

SCHEME A

-continued
SCHEME A

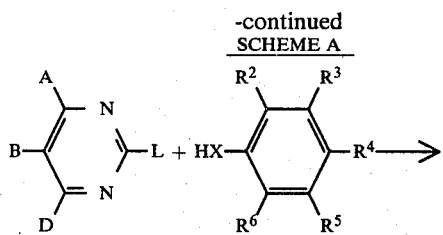

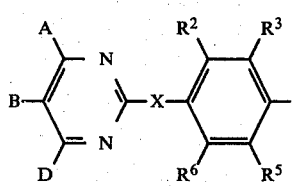

Compounds of formula I wherein one or more of $R^2$, $R^3$, $R^4$, $R^5$ and $R^6$ is the group $YR^1$ and $R^1$ is hydrogen may be prepared from the corresponding compounds of formula I, wherein $R^1$ is an optionally substituted alkyl group, by dealkylation. Compounds of formula I wherein one or more of $R^2$, $R^3$, $R^4$, $R^5$ and $R^6$ is the group $YR^1$ and $R^1$ is hydrogen may also be prepared from the corresponding compounds of formula I wherein $R^1$ is an acyl group, by hydrolytic cleavage of the acyl group.

Compounds of formula I wherein at least one of $R^2$, $R^3$, $R^4$, $R^5$ and $R^6$ is the group $$\underset{\underset{CYR^1}{\|}}{O}$$

wherein Y is oxygen and $R^1$ is hydrogen may be prepared by hydrolysis of the corresponding ester of formula I wherein at least one of $R^2$, $R^3$, $R^4$, $R^5$ and $R^6$ is the ester group $$\underset{\underset{CYR^1}{\|}}{O}$$

wherein Y is oxygen and $R^1$ is a hydrocarbon radical.

Compounds of formula I wherein at least one of $R^2$, $R^3$, $R^4$, $R^5$ and $R^6$ is the group $YR^1$ wherein Y is oxygen and $R^1$ is an optionally substituted group chosen from alkyl, alkenyl, alkynyl and benzyl may be prepared by the alkylation, alkenylation, alkynylation or benzylation respectively of the corresponding compound of formula I wherein at least one of $R^2$, $R^3$, $R^4$, $R^5$ and $R^6$ is the group $YR^1$ wherein Y is oxygen and $R^1$ is hydrogen.

Compounds of formula I wherein at least one of $R^2$, $R^3$, $R^4$, $R^5$ and $R^6$ is the group $$\underset{\underset{CYR^1}{\|}}{O}$$

wherein Y is oxygen and $R^1$ is an optionally substituted group chosen from alkyl, alkenyl, alkynyl, benzyl and phenyl may be prepared by the esterification of the corresponding compound of formula I wherein at least one of $R^2$, $R^3$, $R^4$, $R^5$ and $R^6$ is the group $$\underset{\underset{CYR^1}{\|}}{O}$$

wherein Y is oxygen and $R^1$ is hydrogen with an alkanol, alkenol, alkynol, a benzyl alcohol or a phenol respectively.

Compounds of formula I wherein at least one of the substituents $R^2$, $R^3$, $R^4$, $R^5$ and $R^6$ is hydrogen may be further modified by the replacement of one or more of said hydrogen atoms with an electrophilic group such as, for example, a nitro group or halogen atom, by an electrophilic aromatic substitution reaction.

The condensation reaction illustrated in SCHEME A outlined above preferably is carried out in the presence of an alkaline material and preferably in the presence of a solvent. Suitable alkaline materials include, for example, the alkali and alkaline earth metal hydroxides and carbonates such as sodium hydroxide, potassium hydroxide, sodium carbonate and potassium carbonate. Suitable solvents include ketones such as, for example, acetone, methyl ethyl ketone and methyl isobutyl ketone, and dipolar aprotic solvents such as, for example, dimethylformamide, dimethylacetamide, dimethylsulfoxide, N-methylpyrrolidone, hexamethylphosphoramide and sulfolan.

The reaction conditions required to effect the condensation reaction illustrated in SCHEME A and outlined above vary according to the nature of the reactants, the alkaline material and the solvent used. In general the reaction is facilitated by the application of heat and usually a reaction temperature in the range of 40° to 150° C. and reaction time of between 0.5 and 20 hours is satisfactory. However, high or lower reaction temperatures and/or shorter or longer reaction times may be used if desired.

The dealkylation reaction outlined above may be effected using a variety of reagents known in the art. For example, aryl-alkyl ethers may be cleaved using reagents such as pyridine hydrochloride, hydriodic acid, hydrobromic acid, sodium thioethoxide in dimethylformamide, acetyl p-toluenesulphonate, sodium or potassium iodide in formic or acetic acid, lithium iodide in 2,4,6-collidine and borontribromide. Reaction times and reaction conditions vary widely depending on the dealkylation agent used and the ether to be cleaved. The reaction conditions generally employed when using the above "ether-cleavage" reagents are known in the art and may be adapted without undue experimentation to effect the "ether-cleavage" reactions outlined above.

The hydrolytic cleavage reactions outlined above may be effected using any of the conventional methods in the art for the hydrolytic cleavage of esters and thioesters. In general hydrolytic cleavage by alkaline hydrolysis is preferred.

Generally speaking the process of the invention is effective in inhibiting the growth of, severely damaging, or killing plants both when the compositions are applied directly to the plants (post-emergence application) and when the compositions are applied to the soil before the emergence of the plants (pre-emergence application). However, in general the compounds are more effective when applied to the plant growth medium before the emergence of the plants.

In the process of the invention the compounds of formula I are preferably used in the form of a composition comprising a compound of formula I in admixture with a carrier comprising a solid or liquid diluent. Therefore, in yet a further aspect of the invention provides plant growth inhibiting, plant damaging, or plant killing compositions comprising a novel compound of formula I as hereinbefore defined and an inert carrier therefor.

Compositions according to the invention include both dilute compositions, which are ready for immediate use, and concentrated compositions, which require to be diluted before use, usually with water. Preferably the compositions contain from 0.01% to 90% by weight of the active ingredient. Dilute compositions ready for use preferably contain from 0.01 to 2% of active ingredient, while concentrated compositions may contain from 20 to 90% of active ingredient, although from 20 to 70% is usually preferred.

Solid compositions may be in the form of granules, or dusting powders wherein the active ingredient is mixed with a finely divided solid, e.g. kaolin, bentonite, kieselguhr, dolomite, calcium carbonate, talc, powdered magnesia, Fuller's earth and gypsum. They may also be in the form of dispersible powders or grains, comprising a wetting agent to facilitate the dispersion of the powder or grains in liquid. Solid compositions in the form of a powder may be applied as foliar dusts.

Liquid compositions may comprise a solution or dispersion of an active ingredient in water optionally containing a surface-active agent, or may comprise a solution or dispersion of an active ingredient in a water-immiscible organic solvent which is dispersed as droplets in water.

Surface-active agents may be of the cationic, anionic, or non-ionic type. The cationic agents are, for example, quaternary ammonium compounds (e.g. cetyltrimethylammonium bromide). Suitable anionic agents are soaps; salts of aliphatic mono esters of sulphuric acid, for example sodium lauryl sulphate; and salts of sulphonated aromatic compounds, for example sodium dodecylbenzenesulphonate, sodium, calcium, and ammonium lignosulphate, butylnaphthalene sulphonate, and a mixture of the sodium salts of diisopropyl- and triisopropyl-naphthalenesulphonic acid. Suitable non-ionic agents are the condensation products of ethylene oxide with fatty alcohols such as oleyl alcohol and cetyl alcohol, or with alkylphenols such as octyl- or nonyl-phenol or octylcresol. Other non-ionic agents are the partial esters derived from long chain fatty acids and hexitol anhydrides, for example sorbitan monolaurate; the condensation products of the partial ester with ethylene oxide; and the lecithins.

The aqueous solutions or dispersions may be prepared by dissolving the active ingredient in water or an organic solvent optionally containing wetting or dispersing agent(s) and then, when organic solvents are used, adding the mixture so obtained to water optionally containing wetting or dispersing agent(s). Suitable organic solvents include, for example, ethylene dichloride, isopropyl alcohol, propylene glycol, diacetone alcohol, toluene, kerosene, methylnaphthalene, the xylenes and trichloroethylene.

The compositions for use in the form of aqueous solutions or dispersions are generally supplied in the form of a concentrate containing a high proportion of the active ingredient, and the concentrate is then diluted with water before use. These concentrates are usually required to withstand storage for prolonged periods and after such storage, to be capable of dilution with water to form aqueous preparations which remain homogeneous for a sufficient time to enable them to be applied by conventional spray equipment. Concentrates conveniently contain 20–90%, preferably 20–70%, by weight of the active ingredient(s). Dilute preparations ready for use may contain varying amounts of the active ingredient(s), depending upon the intended purpose; amounts of 0.01% to 10.0% and preferably 0.1% to 2%, by weight of active ingredient(s) are normally used.

A preferred form of concentrated composition comprises the active ingredient which has been finely divided and which has been dispersed in water in the presence of a surface-active agent and a suspending agent. Suitable suspending agents are hydrophilic colloids and include, for example, polyvinylpyrrolidone and sodium carboxymethylcellulose, and the vegetable gums, for example gum acacia and gum tragancanth. Preferred suspending agents are those which impart thixotropic properties to, and increase the viscosity of the concentrate. Examples of preferred suspending agents include hydrated colloidal mineral silicates, such as montmorillonite, beidellite, nontronite, hectorite, saponite, and saucorite. Bentonite is especially preferred. Other suspending agents include cellulose derivatives and polyvinyl alcohol.

In the process of the invention the compounds of formula I show herbicidal activity against a wide variety of plants. Certain of the compounds, for example, 3, 7, 8 and 120 show a broad spectrum of activity. However, other compounds show selectivity.

Therefore, in yet a further aspect the invention provides a process for selectively controlling the growth of weeds in crops which process comprises applying to the crop, or to the growth medium of the crop, a compound of formula I, as hereinbefore defined, in an amount sufficient to severely damage or kill the weeds but insufficient to damage the crop substantially.

The compounds 20, 22, 72, 79, 87, 88, 116 and 131 have shown particularly good selectivity for the killing of weeds in sunflower crops, while the compounds 14, 46, 52, 54, 55, 64 and 69 have shown particularly good selectivity for the control of weeds in cotton crops. The compounds 47, 108, 109 and 111 have shown particularly good selectivity for the control of weeds in wheat crops.

The rate of application of the active ingredient will depend on a number of factors including, for example, the compound chosen for use, the identity of the plants whose growth is to be inhibited, the formulation selected for use and whether the compound is to be applied for foilage or root uptake. As a general guide, however, an application rate of from 0.01 to 10 kilograms per hectare is suitable while from 0.1 to 5 kilograms per hectare may be preferred. The skilled worker in the art will readily be able to ascertain suitable application rates by standardised routine methods without undue experimentation.

It is to be understood that the compositions of this invention may comprise, in addition to one or more compounds of the invention, one or more compounds not of this invention which have biological activity.

The invention is now illustrated by, but by no means limited to, the following examples.

EXAMPLE 1

Preparation of 5-Bromo-2-(4-methoxyphenoxy)-pyrimidine (1)

5-Bromo-2-chloropyrimidine (3.0 g), p-methoxyphenol (2.5 g), methyl ethyl ketone (50 ml—dried over anhydrous potassium carbonate) and anhydrous potassium carbonate (2.5 g) were heated under reflux with stirring for 6 hours. The solvent was evaporated under reduced pressure, the residue treated with water and the precipitated compound collected by filtration. The product was treated with 5% sodium hydroxide aqueous solution and the mixture stirred for approximately 30 minutes. The solid was collected by filtration, washed with water and recrystallised from methanol/water to give the title compound (3.4 g), m.p. 92° C.

EXAMPLE 2

Preparation of 2-(3-chlorophenylthio)pyrimidine (16)

A solution of 3-chloroaniline (5.0 g) in 1.5 M hydrochloric acid (100 ml) was diazotised by the gradual addition of a solution of sodium nitrate (3.0 g) in water (6 ml) at 0° C. Sodium bicarbonate (7.5 g) was then added to the solution and the whole reaction mixture was added rapidly with stirring to a solution of 2-mercaptopyrimidine (4.5 g) in water (3 l). When the addition of the diazonium salt solution was completed, 10 ml of a 15% solution of sodium carbonate was added causing precipitation of a colourless solid. The solid was collected by filtration and allowed to stand overnight during which time it decomposed to an oil which was purified by chromatography (70 g silica, chloroform elution). The title compound was obtained as a red oil (2.5 g, 29%) and identified by its pmr spectrum.

EXAMPLE 3

Preparation of 5-chloro-2-[3-(2,4-dichlorobenzyloxy)phenoxy]-pyrimidine (110)

A solution of 3-[5-chloro-2-pyrimidyloxy]phenol (1.11 g), 2,4 dichlorobenzylchloride (0.98 g), potassium carbonate (0.76 g) and sodium iodide (0.075 g) in methyl ethyl ketone (25 ml) was refluxed for four hours. After dilution with water, the reaction mixture was extracted into chloroform and the extracts dried over anhydrous magnesium sulphate. Removal of the solvent under vacuum gave a white solid which was recrystallised from ethanol to give 1.45 g (77%) of the title compound, mp 110° C.

EXAMPLE 4

Preparation of 3-(5-chloro-2-pyrimidyloxy)phenyltrimethylammonium iodide (81)

A solution of 5-chloro-2-(3-dimethylaminophenoxy)pyrimidine (3.75 g) and methyl iodide (4.50 g) in ether (25 ml) was stirred at room temperature for one week. Filtration of the ether solution gave 2.75 g (47%) of the title compound, mp 155° C.

EXAMPLE 5

Preparation of 4-(5-Bromo-2-pyrimidyloxy)phenol (171)

5-Bromo-2-(4-methoxyphenoxy)pyrimidine (2.4 g) was dissolved in methylene chloride (50 ml) and the solution cooled to a temperature of −70° C. Boron tribromide (12.7 g) was added dropwise to the stirred solution, the temperature of the solution being maintained at −65° to −75° C. On completion of the addition the reaction mixture was stirred for a further one hour at a temperature of −65° to −75° C. and then the temperature of the reaction mixture was allowed to rise slowly to room temperature. The reaction mixture was added cautiously, in small portions, to water and the methylene chloride removed by heating the mixture on a water bath. The aqueous suspension was cooled to a temperature of 20° C., the solid was collected by filtration, washed with water and recrystallised from methanol/water to give 4-(5-bromo-2-pyrimidyloxy)phenol (2.1 g) m.p. 178° C.

EXAMPLE 6

Preparation of 5-chloro-2-(3-ethoxy-4-nitrophenoxy)pyrimidine (91)

2-Nitro-5-(5-chloro-2-pyrimidyloxy)phenol (0.65 g), ethyl iodide (2 ml), potassium carbonate (0.35 g) and methyl ethyl ketone (20 ml) were heated together under reflux with stirring for 15 hours. The solvent was evaporated under reduced pressure and the residue was partitioned between water and chloroform. The chloroform extracts were dried and evaporated under reduced pressure to give a pale yellow solid which was recrystallized from ethanol to give the title compound as pale yellow needles (0.54 g), m.p. 114°–115° C.

EXAMPLE 7

Preparation of 5-chloro-2-(3-ethoxycarbonyl-4-nitrophenoxy)pyrimidine (102)

Potassium nitrate (1.01 g) was added slowly with stirring to a mixture of 5-chloro-2-(3-ethoxy-carbonylphenoxy)pyrimidine (2.79 g) in ethylene dichloride (10 ml) and concentrated sulphuric acid (2 ml) at 0° C. The reaction mixture was stirred for 1 hour at 0° C. and then poured onto ice and extracted with chloroform. The chloroform extract was dried and evaporated to give a nearly colourless solid (2.4 g), m.p. 86° C., which was characterised by its pmr spectrum as the title compound.

EXAMPLE 8

Preparation of 5-trichloromethyl-2-(3-trifluoromethyl-phenoxy)-pyrimidine (133)

5-Methyl-2-(3-trifluoromethylphenoxy)pyrimidine (5.14 g) was dissolved in 550 ml of dry carbon tetrachloride and transferred to a photochemical reaction vessel. Dry hydrogen chloride gas was bubbled through a sintered-glass inlet for 10 minutes until the solution absorbed no more hydrogen chloride and a heavy white precipitate of the hydrochloride salt had formed. The carbon tetrachloride suspension was then brought to reflux under anhydrous conditions and dry chlorine gas was bubbled through the suspension which was irradiated by a 250 watt infrared lamp. The reaction was followed by thin layer chromatography and the reaction was terminated after 70 minutes. The title compound was obtained as an oil on evaporation of the carbon tetrachloride, yield 7.2 g (≈100%).

EXAMPLE 9

Preparation of 5-chloro-2-[3-(2,2-dibromovinyl)phenoxy]-pyrimidine (156)

Carbon tetrabromide (3.32 g) was added with stirring to a solution of triphenylphosphine (5.24 g) in methylne chloride (20 ml) at 20° C. 5-Chloro-2-(3-formylphenoxy)-pyrimidine (1.8 g) was added immediately to the warm orange solution causing the colour to fade rapidly. After 2 hours at 20° C. the reaction mixture was washed with water and then the organic layer was dried and concentrated to a thick syrup. Extraction of this syrup with n-hexane (4×50 ml), followed by evaporation of the n-hexane gave a colourless oil (3 g). The oil was chromatographed on a column of silica gel (50 g) and elution with chloroform gave the title compound, in the first fractions, as a colourless crystalline solid (1.95 g), m.p. 68° C.

EXAMPLE 10

Preparation of 2-nitro-5-(5-chloro-2-pyrimidyloxy)-phenol (164)

Fuming nitric acid (1.3 g) was added slowly to a stirred suspension of 3-(5-chloro-2-pyrimidyloxy)-phenol (2.2 g) in diethyl ether (20 ml) at 20° C. The temperature rose to 30° C. and the resultant orange solution was allowed to stand for 48 hr before the addition of water and extraction with chloroform (100 ml). The chloroform extracts were dried and evaporated to give a pale yellow crystalline solid (1.3 g). Chromatography on a column of silica gel (80 g) with chloroform elution gave the title compound as a pale yellow-solid from the first fraction (0.7 g, 28%). The compound was identified from its pmr spectrum.

EXAMPLE 11

The compounds detailed in Tables IIa, IIb and IIc below were prepared following essentially the same procedure as that described in the cited method of preparation and detailed in the corresponding numbered Examples 1 to 10 above. The compounds were characterised by melting point (Table IIa), proton magnetic resonance spectrascopy (Table IIb) or mass spectrum (Table IIc).

TABLE IIa

| Compound No | Preparative Method No | m.p. °C. | Compound No | Preparative Method No | m.p. °C. |
|---|---|---|---|---|---|
| 1 | 1 | 92 | 52 | 1 | 85 |
| 2 | 1 | 110 | 53 | 1 | 118 |
| 4 | 1 | 110 | 54 | 1 | 42 |
| 5 | 1 | 90 | 57 | 1 | 77 |
| 8 | 1 | 65 | 58 | 1 | 67 |
| 9 | 1 | 99 | 59 | 1 | 75 |
| 10 | 1 | 105 | 63 | 1 | 99 |
| 13 | 1 | 112 | 64 | 1 | 73 |
| 17 | 1 | 49 | 65 | 1 | 57 |
| 18 | 1 | 130 | 66 | 1 | 84 |
| 20 | 1 | 96 | 67 | 1 | 70 |
| 21 | 1 | 71 | 68 | 1 | 78 |
| 22 | 1 | 57 | 73 | 1 | 90 |
| 23 | 1 | 127 | 75 | 1 | 97 |
| 24 | 1 | 93 | 76 | 1 | 59 |
| 25 | 1 | 45 | 79 | 3 | 50 |
| 26 | 1 | 123 | 80 | 1 | 161 |
| 27 | 1 | 69 | 81 | 4 | 155 |
| 29 | 1 | 83 | 83 | 3 | 78 |
| 31 | 1 | 101 | 85 | 1 | 74 |
| 32 | 1 | 99 | 86 | 1 | 128 |
| 37 | 1 | 96 | 89 | 3 | 83 |
| 40 | 1 | 143 | 90 | 3 | 78 |
| 41 | 1 | 81 | 91 | 6 | 115 |
| 42 | 1 | 48 | 92 | 1 | 75 |
| 43 | 1 | 143 | 93 | 1 | 88 |
| 44 | 1 | 122 | 96 | 1 | 78 |
| 45 | 1 | 67 | 97 | 1 | 129 |
| 46 | 1 | 59 | 101 | 1 | 102 |
| 47 | 1 | 94 | 102 | 7 | 86 |
| 48 | 1 | 160 | 104 | 1 | 98 |
| 49 | 1 | 58 | 105 | 1 | 62 |
| 106 | 1 | 60 | 142 | 3 | 92 |
| 107 | 1 | 104 | 144 | 1 | 69 |
| 108 | 3 | 50 | 148 | 3 | 132 |
| 109 | 3 | 70 | 149 | 1 | 86 |
| 110 | 3 | 110 | 152 | 1 | 99 |
| 111 | 1 | 78 | 154 | 1 | 146 |
| 114 | 3 | 100 | 156 | 9 | 68 |
| 115 | 1 | 120 | 158 | 1 | 71 |
| 116 | 3 | 55 | 160 | 1 | 126 |
| 118 | 1 | 112 | 162 | 5 | 130 |
| 121 | 3 | 50 | 167 | 1 | 144 |
| 123 | 1 | 79 | 168 | 5 | 190 |
| 125 | 1 | 69 | 170 | 5 | 183 |
| 126 | 3 | 102 | 171 | 5 | 178 |
| 128 | 1 | 67 | 172 | 10 | 181 |
| 129 | 1 | 112 | 173 | 5 | 165 |
| 130 | 1 | 64 | 174 | 5 | 119 |
| 136 | 3 | 159 | 175 | 5 | 65 |
| 137 | 1 | 68 | 176 | 5 | 126 |
| 141 | 3 | 105 | 177 | 5 | 195 |

TABLE IIb

| Compound No | Preparative Method No | Partial PMR Spectrum (Chemical Shift in δ ppm) | | |
|---|---|---|---|---|
| | | Pyrimidyl H | Phenyl H | Other H |
| 3 | 1 | 8.5(s) | 6.5–7.7(m) | 3.8(s, CH$_3$) |
| 7 | 1 | 8.5(s) | 6.1–7.4(m) | 3.7(s, CH$_3$) |
| 11 | 1 | 8.6(s) | 7.1–7.7(m) | |
| 12 | 1 | 8.4(s) | 6.7–7.3(m) | 3.6(s, CH$_3$) |
| 14 | 1 | 8.6(s) | 7.2–7.6(m) | |
| 15 | 1 | 8.65(s) | 7.0–7.3(m) | |
| 16 | 2 | 8.4(d); 6.9(d) | 7.1–7.8(m) | |
| 19 | 1 | 8.5(s) | 6.7–7.5(m) | 3.9(t, CH$_2$); 1.9(m, CH$_2$); 1.1(t, CH$_3$) |
| 28 | 1 | 6.1(d); 8.0(d) | 6.9–7.4(m) | 3.0[(s, N(CH$_3$)$_2$] |
| 30 | 1 | 9.15(s) | 6.7–7.4(m) | 4.4(q, CH$_2$); 1.4(t, CH$_3$) |
| 33 | 1 | 8.6(s) | 7.0–7.5(m) | 2.4(s, CH$_3$) |
| 34 | 1 | 8.2(s) | 7.0–7.4(m) | 3.2[(s, N(CH$_3$)$_2$] |
| 35 | 1 | 8.6(s) | 7.2–7.9(m) | |
| 38 | 1 | 8.6(s) | 7.3–7.6(m) | 2.3(s, CH$_3$) |
| 39 | 1 | 8.5(s) | 6.8–7.4(m) | 1.4(t, CH$_3$); 4.1(q, CH$_2$) |
| 50 | 1 | 8.6(s) | 6.7–7.6(m) | 3.8(s, CH$_3$) |

TABLE IIb-continued

| Compound No | Preparative Method No | Partial PMR Spectrum (Chemical Shift in δ ppm) | | |
|---|---|---|---|---|
| | | Pyrimidyl H | Phenyl H | Other H |
| 51 | 1 | 8.6(s) | 6.8–7.3(m) | 3.9(s, CH$_3$) |
| 55 | 1 | 8.6(s) | 6.8–7.4(m) | 2.7(q, CH$_2$); 1.1(t, CH$_3$) |
| 56 | 1 | 8.6(s) | 7.1–8.4(m) | |
| 60 | 1 | 8.4(s) | 7.0–7.6(m) | |
| 61 | 1 | 8.4(s) | 6.8–7.4(m) | 3.8(s, CH$_3$) |
| 62 | 1 | 8.5(s) | 7.3–7.8(m) | |
| 69 | 1 | 8.5(s) | 7.0–7.4(m) | 2.7–3.2(m, CH); 1.2(d, CH$_3$) |
| 70 | 1 | 8.4(s) | 7.0–7.4(m) | 2.2(s, CH$_3$) |
| 71 | 1 | 8.6(s) | 7.0–7.5(m) | 4.5(q, CH$_2$); 1.4(t, CH$_3$) |
| 72 | 3 | 8.6(s) | 6.8–7.4(m) | 5.2–6.3(m, CH$_2$=CH); 4.5(d, CH$_2$) |
| 74 | 1 | 8.4(s) | 6.7–7.5(m) | 3.8(s, CH$_3$); 2.2(s, CH$_3$) |
| 77 | 1 | 8.4(s) | 6.9–7.5(m) | 2.4(s, CH$_3$); 2.2(s, CH$_3$) |
| 78 | 1 | 8.75(s) | 7.3–7.6(m) | |
| 82 | 1 | 8.6(s) | 7.1–7.5(m) | 2.4(s, CH$_3$) |
| 84 | 1 | 8.5(s) | 6.9(s) | 2.6(q, CH$_2$); 2.3(s, CH$_3$); 1.2(t, CH$_3$) |
| 87 | 3 | 8.4(s) | 6.8–7.4(m) | 5.5(d, CH$_2$=); 4.5(s, CH$_2$) |
| 88 | 3 | 8.6(s) | 6.7–7.4(m) | 4.1(t, CH$_2$); 3.7(t, CH$_2$); 2.2(m, CH$_2$) |
| 94 | 1 | 8.0(s) | 7.1–7.6(m) | 5.6(bs, NH); 3.05(d, CH$_3$) |
| 95 | 1 | 8.0(s) | 7.5(bm) | 5.5(bs, NH); 3.0(d, CH$_3$) |
| 98 | 1 | 8.4(s) | 6.6–7.2(m) | 3.7(s, CH$_3$); 2.5(q, CH$_2$); 1.2(t, CH$_3$) |
| 99 | 1 | 8.5(s) | 7.0–7.3(m) | 3.7(s, CH$_3$) |
| 100 | 1 | 8.5(s) | 6.7–7.3(m) | 5.5–6.2(m, CH$_2$=CH) 4.8–5.1); 3.3(d, CH$_2$) |
| 103 | 1 | 7.2(d); 8.5(d) | 7.3–7.6(m) | |
| 113 | 1 | 8.3(s) | 7.5(bm) | 2.4(s, CH$_3$) |
| 117 | 1 | 8.6(s) | 7.0–7.8(m) | 5.04, 5.94, 6.84 (all t, CH) |
| 119 | 1 | 8.5(s) | 6.85(bm) | 2.3(s, CH$_3$) |
| 122 | 1 | 8.1(s) | 7.1–7.5(m) | 2.9(s, CH$_3$) |
| 124 | 1 | 7.6(d); 8.7(d) | 7.1–7.5(m) | |
| 127 | 1 | 8.9(s) | 7.2–7.7(m) | 3.0–3.6(m, CH); 2.7(s, CH$_3$); 1.7(d, CH$_3$) |
| 131 | 1 | 8.55(s) | 7.1–7.8(m) | 5.16, 6.06, 6.96(all t, CH); 2.3(s, CH$_3$) |
| 132 | 1 | 8.5(s) | 6.4–7.3(m) | 5.7–6.2(m, CH); 5.4(t, CH$_2$); 4.5(d, CH$_2$) |
| 133 | 8 | 9.1–9.4(m) | 7.5–7.8(m) | |
| 134 | 1 | 8.5(s) | 7.3(bm) | 3.8(s, CH$_3$) |
| 135 | 1 | 8.6(s) | 7.1–8.0(m) | |
| 138 | 1 | 8.7(s) | 7.2–7.7(m) | 4.5(q, CH$_2$); 1.4(t, CH$_3$) |
| 139 | 1 | 8.8(d); 7.5(d) | 7.1–7.6(m) | |
| 140 | 3 | 8.5(s) | 6.4–7.0(m) | 4.1–4.7(m, CH); 1.3(d, CH$_3$) |
| 143 | 1 | 8.9(d); 7.8(d) | 7.3–7.7(m) | 6.9, 6.0, 5.1(all t, CH) |
| 145 | 1 | 8.45(s) | 7.15–7.7(m) | 2.3(s, CH$_3$) |
| 146 | 1 | 8.6(s) | 7.1–7.65(m) | |
| 147 | 1 | 8.7(s) | 7.1–7.5(m) | 5.1, 6.0, 6.9(all t, CH) |
| 150 | 1 | 8.5(s) | 7.2–7.5(m) | 6.9, 6.0, 5.1(all t, CH); 2.6(q, CH$_2$); 1.3(t, CH$_3$) |
| 151 | 1 | 8.5(s) | 6.8–7.5(m) | |
| 153 | 1 | 8.8(d); 7.8(d) | 7.1–7.8(m) | |
| 155 | 1 | 8.4(s) | 7.25–7.55(m) | 6.95, 6.05, 5.15(all t, CH); 4.15(q, CH$_2$); 1.4(t, CH$_3$) |
| 157 | 1 | 8.3(s) | 6.9–7.7(m) | |
| 159 | 1 | 8.6(s) | 6.9–7.5(m) | |
| 161 | 1 | 8.6(s) | 6.9–7.4(m) | |
| 163 | 10 | 8.6(s) | 6.8–7.2(m); 8.3(m) | |
| 164 | 10 | 8.6(s) | 7.2–7.6(m); 8.0(m) | |
| 166 | 1 | 8.6(s) | 7.0–7.3(m) | |
| 169 | 5 | 8.5(s) | 6.3–7.2(m) | |

TABLE IIc

| Compound No | Preparative Method No | Mass Spectrum m/e |
|---|---|---|
| 6 | 1 | 328(M+), 202 (100%) |
| 112 | 1 | 308(M+), 280, 273, 206, 179, |
| 120 | 1 | 332(M+), 205, 170, 142, 76, 63, 50 |

EXAMPLE 12

Compositions suitable for use in evaluating pre-emergence and post-emergence herbicidal activity were prepared as follows.

A concentrated composition was prepared by adding 4 parts by weight of the active ingredient to 96 parts by weight of "Lubrol" E (a Registered Trade Mark for a condensation product of alkylphenol with ethylene oxide) and the mixture was ball-milled to produce a stable suspension. The concentrated suspension was then diluted with water to give an aqueous composition suitable for use in the evaluation of the herbicidal activity of the active ingredient.

EXAMPLE 13

The pre-emergent herbicidal activity of the compositions prepared according to Example 12 were assessed by the following procedure.

The seeds of the test species were sprinkled onto the surface of soil in each of five seed boxes and covered with a thin layer of sand. Each of four boxes was then sprayed with a quantity of a composition of the invention and the remaining box was sprayed with an equivalent volume of water for comparison purposes. The boxes were then lightly watered with an overhead spray and placed in a glasshouse to encourage germination of the seeds. Three weeks later the boxes were removed from the glasshouse and the effect of the treatment was visually assessed. The results are presented in Table III wherein the damage to the plants is rated on a scale of 0 to 3 where 0 represents 0 to 25% damage and 3 represents 90 to 100% kill.

TABLE III

| | PRE-EMERGENCE HERBICIDAL ACTIVITY | | | | | | | | |
|---|---|---|---|---|---|---|---|---|---|
| Compound No | APPLICATION Rate (kg/ha) | Wh | Ot | Rg | Jm | P | Ip | Ms | Sf |
| 3 | 5 | 3 | 1 | 3 | 3 | 1 | 2 | 3 | 0 |
| 3 | 1 | 0 | 1 | 2 | 2 | 0 | 2 | 1 | 1 |
| 7 | 5 | 2 | 2 | 3 | 3 | 0 | 3 | 3 | 3 |
| 7 | 1 | 0 | — | 2 | 2 | 0 | 2 | 1 | — |
| 13 | 5 | 1.5 | 1 | 3 | 3 | 0 | 0 | 0 | 0 |
| 13 | 1 | 0 | 0 | 3 | 3 | 0 | 0 | 0 | 0 |
| 14 | 5 | 3 | 3 | 3 | 3 | 3 | 3 | 3 | 2 |
| 14 | 1 | 3 | 3 | 3 | 3 | 2 | 3 | 3 | 0 |
| 15 | 5 | 3 | 3 | 3 | 3 | 2 | 3 | 3 | 0 |
| 15 | 1 | 1 | 1 | 2 | 2 | 2 | 0 | 1 | 0 |
| 19 | 5 | 2 | 3 | 3 | 3 | 0 | 1 | 1 | 0 |
| 19 | 1 | 1 | 1 | 1 | 3 | 0 | 0 | 0 | 0 |
| 20 | 5 | 3 | 3 | 3 | 3 | 1 | 3 | 3 | 0 |
| 20 | 1 | 1 | 1 | 3 | 3 | 0 | 2 | 3 | 0 |
| 20 | 0.5 | 0 | 0 | 1 | 2 | 0 | 0 | 0 | 0 |
| 22 | 5 | 3 | 3 | 3 | 3 | 3 | 3 | 3 | 1 |
| 22 | 1 | 3 | 2 | 3 | 0 | 3 | 3 | 2 | 0 |
| 22 | 0.5 | 0 | 0 | 0 | 2 | 0 | 0 | 0 | 0 |
| 23 | 5 | 2 | 2 | 3 | 3 | 0 | 0 | 0 | 0 |
| 23 | 1 | 0 | 0 | 2 | 3 | 0 | 0 | 0 | 0 |
| 8 | 5 | 3 | 3 | 3 | 3 | 3 | 3 | 3 | 3 |
| 8 | 1 | 1 | 3 | 3 | 3 | 2 | — | 3 | — |
| 35 | 5 | 3 | 3 | 3 | 3 | 3 | 3 | 3 | 0 |
| 35 | 1 | 1 | 1 | 2 | 3 | 0 | 3 | 2 | 0 |
| 43 | 5 | 0 | 0 | 0 | 3 | 3 | 3 | 3 | 3 |
| 43 | 1 | 0 | 0 | 0 | 2 | 0 | 2 | 1 | 0 |
| 47 | 5 | 0 | 0 | 3 | 3 | 0 | 0 | 0 | 0 |
| 47 | 1 | 0 | 0 | 3 | 3 | 0 | 0 | 0 | 0 |
| 50 | 5 | 2 | 3 | 3 | 3 | 0 | 0 | 2 | 0 |
| 50 | 1 | 1 | 1 | 3 | 3 | 0 | 0 | 2 | 0 |
| 54 | 5 | 3 | 3 | 3 | 3 | 3 | 3 | 3 | 0 |
| 54 | 1 | 0 | 1 | 2 | 2 | 0 | 1 | 0 | 0 |
| 64 | 5 | 2 | 3 | 3 | 3 | 0 | 0 | 0 | 0 |
| 64 | 1 | 1 | 0 | 2 | 3 | 0 | 0 | 0 | 0 |
| 68 | 5 | 1 | 0 | 3 | 3 | 0 | 0 | 1 | 0 |
| 68 | 1 | 1 | 0 | 2 | 3 | 0 | 0 | 0 | 0 |
| 70 | 5 | 2 | 2 | 3 | 3 | 0 | 0 | 0 | 0 |
| 70 | 1 | 2 | 1 | 2 | 3 | 0 | 0 | 0 | 0 |
| 72 | 5 | 2 | 2 | 3 | 3 | 0 | 2 | 3 | 0 |
| 72 | 1 | 1 | 2 | 2 | 3 | 0 | 0 | 0 | 0 |
| 78 | 5 | 2 | 2 | 3 | 3 | 1 | 2 | 3 | 0 |
| 78 | 1 | 2 | 0 | 2 | 2 | 0 | 0 | 2 | 0 |
| 79 | 5 | 2 | 2 | 3 | 3 | 1 | 3 | 3 | 0 |
| 79 | 1 | 0 | 0 | 2 | 3 | 0 | 2 | 2 | 0 |
| 87 | 5 | 3 | 3 | 3 | 3 | 0 | 2 | 3 | 0 |
| 87 | 1 | 2 | 1 | 3 | 3 | 0 | 1 | 0 | 0 |
| 88 | 5 | 2 | 3 | 3 | 3 | 0 | 0 | 3 | 0 |
| 88 | 1 | 0 | 0 | 3 | 3 | 0 | 0 | 2 | 0 |
| 90 | 5 | 1 | 1 | 3 | 2 | 0 | 0 | 0 | 0 |
| 90 | 1 | 0 | 0 | 3 | 0 | 0 | 0 | 0 | 0 |
| 91 | 5 | 2 | 2 | 3 | 3 | 0 | 0 | 0 | 0 |
| 91 | 1 | 0 | 0 | 3 | 3 | 0 | 0 | 0 | 0 |
| 106 | 5 | 1 | 3 | 3 | 3 | 0 | 0 | 0 | 0 |
| 106 | 1 | 0 | 0 | 2 | 2 | 0 | 0 | 0 | 0 |
| 108 | 5 | 2 | 2 | 3 | 3 | 0 | 1 | 2 | 0 |
| 108 | 1 | 1 | 1 | 3 | 3 | 0 | 0 | 1 | 0 |
| 109 | 5 | 1 | 2 | 3 | 3 | 0 | 0 | 0 | 0 |
| 109 | 1 | 0 | 1 | 3 | 2 | 0 | 0 | 0 | 0 |
| 111 | 5 | 0 | 0 | 3 | 3 | 0 | 0 | 0 | 0 |
| 111 | 1 | 0 | 0 | 2 | 2 | 0 | 0 | 0 | 0 |
| 112 | 5 | 2 | 2 | 3 | 3 | 1 | 3 | 3 | 3 |
| 112 | 1 | 1 | 2 | 3 | 3 | 0 | 1 | 2 | 0 |
| 116 | 5 | 2 | 3 | 3 | 3 | 0 | 1 | 2 | 0 |
| 116 | 1 | 1 | 2 | 3 | 3 | 0 | 2 | 1 | 0 |
| 117 | 5 | 3 | 3 | 3 | 3 | 3 | 3 | 3 | 1 |
| 117 | 1 | 3 | 3 | 3 | 3 | 2 | 3 | 3 | 0 |
| 118 | 5 | 1 | 2 | 3 | 3 | 0 | 0 | 1 | 0 |
| 118 | 1 | 0 | 0 | 3 | 3 | 0 | 0 | 0 | 0 |
| 120 | 5 | 3 | 3 | 3 | 3 | 3 | 3 | 3 | 1 |
| 120 | 1 | 1 | 3 | 3 | 3 | 1 | 3 | 3 | 0 |
| 120 | 0.5 | 2 | 3 | 3 | 3 | 1 | 2 | 2 | 0 |
| 121 | 5 | 2 | 1 | 3 | 3 | 0 | 0 | 1 | 0 |
| 121 | 1 | 0 | 0 | 3 | 2 | 0 | 0 | 0 | 0 |
| 131 | 5 | 3 | 3 | 3 | 3 | 1 | 3 | 1 | 0 |
| 131 | 1 | 2 | 2 | 3 | 3 | 0 | 3 | 0 | 0 |
| 131 | 0.5 | 2 | 2 | 2 | 3 | 0 | 2 | 0 | 0 |

The names of the test plants were as follows:

| Wh | Wheat | P | Peas |
|---|---|---|---|
| Ot | Wild Oats | Ip | Ipomea |
| Rg | Ryegrass | Ms | Mustard |
| Jm | Japanese millet | Sf | Sunflower |

EXAMPLE 14

The post-emergence herbicidal activity of the compositions prepared according to Example 12 was assessed by the following procedure.

The seeds of the test species were sprinkled onto the surface of soil in seed boxes and covered with a thin layer of sand. The boxes were lightly watered with an overhead spray and placed in a glass house for one week to permit germination of the seeds and plant growth to a height of 4 to 5 inches. The boxes were then removed from the glass house and sprayed with a composition of the invention. For comparison purposes at least one box containing one week old seedlings was sprayed lightly with water only. After spraying the boxes were returned to the glass house for a further 3 weeks and the effect of the treatment was visually assessed. The results are presented in Table IV wherein the damage to the plants is rated on a scale of 0 to 3 where 0 represents 0 to 25% damage, and 3 90 to 100% kill.

TABLE IV

POST-EMERGENCE HERBICIDAL ACTIVITY

| Compound No | APPLI-CATION Rate (kg/ha) | TEST PLANT |||||||
|---|---|---|---|---|---|---|---|---|
| | | Wh | Ot | Rg | Jm | P | Ip | Ms | Sf |
| 3 | 5 | 3 | 3 | 3 | 3 | 1 | 3 | 3 | 2 |
| 3 | 1 | 2 | 3 | 3 | 3 | 0 | 2 | 2 | 2 |
| 7 | 5 | 3 | 3 | 3 | 3 | 1 | 2 | 3 | 0 |
| 7 | 1 | 0 | 0 | — | 3 | 0 | 2 | 0 | 0 |
| 13 | 5 | 3 | 1 | 2 | 3 | 0 | 0 | 2 | 0 |
| 13 | 1 | 0 | 1 | 1 | 2 | 0 | 0 | 2 | 0 |
| 14 | 5 | 3 | 3 | 3 | 3 | 3 | 2 | 2 | 2 |
| 14 | 1 | 3 | 3 | 3 | 2 | 3 | 0 | 0 | — |
| 15 | 5 | 3 | 2 | 3 | 3 | 2 | 3 | 3 | 2 |
| 15 | 1 | 1 | 1 | 3 | 3 | 2 | 3 | 2 | 0 |
| 19 | 5 | 2 | 3 | 3 | 3 | 0 | 2 | 2 | 0 |
| 19 | 1 | 0 | 1 | 2 | 3 | 0 | 0 | 0 | 0 |
| 20 | 5 | 3 | 3 | 3 | 3 | 2 | 3 | 3 | 0 |
| 20 | 1 | 2 | 3 | 3 | 3 | 0 | 3 | 3 | 0 |
| 20 | 0.5 | 1 | 0 | 1 | 3 | 0 | 0 | 3 | 0 |
| 22 | 5 | 3 | 3 | 3 | 3 | 3 | 3 | 3 | 1 |
| 22 | 1 | 2 | 3 | 3 | 3 | 3 | 3 | 3 | 0 |
| 22 | 0.5 | 1 | 2 | 3 | 3 | 0 | 3 | 3 | 0 |
| 23 | 5 | 0 | 1 | 3 | 3 | 0 | 2 | 2 | 0 |
| 23 | 1 | 0 | 1 | 2 | 3 | 0 | 1 | 2 | 0 |
| 8 | 5 | 3 | 3 | 3 | 3 | 3 | 3 | 3 | 3 |
| 8 | 1 | 2 | 3 | 3 | 3 | 2 | 3 | 2 | — |
| 35 | 5 | 3 | 3 | 3 | 3 | 0 | 0 | 0 | 0 |
| 35 | 1 | 1 | 1 | 2 | 2 | 0 | 0 | 0 | 0 |
| 43 | 5 | 0 | 0 | 0 | 2 | 3 | 3 | 3 | 2 |
| 43 | 1 | 0 | 0 | 0 | 0 | 3 | 3 | 3 | 0 |
| 47 | 5 | 2 | 1 | 3 | 3 | 0 | 2 | 2 | 0 |
| 47 | 1 | 0 | 0 | 3 | 3 | 0 | 0 | 0 | 0 |
| 50 | 5 | 1 | 2 | 3 | 3 | 0 | 3 | 3 | 1 |
| 50 | 1 | 0 | 0 | 2 | 3 | 0 | 2 | 3 | 0 |
| 54 | 5 | 2 | 2 | 2 | 2 | 0 | 0 | 0 | 0 |
| 54 | 1 | 1 | 0 | 1 | 1 | 0 | 0 | 0 | 0 |
| 64 | 5 | 2 | 3 | 3 | 3 | 0 | 3 | 3 | 0 |
| 64 | 1 | 1 | 1 | 2 | 3 | 0 | 0 | 0 | 0 |
| 68 | 5 | 1 | 1 | 3 | 3 | 0 | 0 | 0 | 0 |
| 68 | 1 | 0 | 0 | 0 | 2 | 0 | 0 | 0 | 0 |
| 70 | 5 | 3 | 3 | 3 | 3 | 0 | 0 | 0 | 0 |
| 70 | 1 | 0 | 0 | 3 | 3 | 0 | 0 | 0 | 0 |
| 72 | 5 | 2 | 2 | 2 | 3 | 0 | 0 | 0 | 0 |
| 72 | 1 | 1 | 1 | 2 | 3 | 0 | 0 | 0 | 0 |
| 78 | 5 | 2 | 2 | 3 | 3 | 0 | 0 | 0 | 0 |
| 78 | 1 | 0 | 0 | 0 | 0 | 0 | 0 | 0 | 0 |
| 79 | 5 | 2 | 2 | 3 | 3 | 0 | 3 | 3 | 0 |
| 79 | 1 | 2 | 2 | 2 | 3 | 0 | 0 | 0 | 0 |
| 87 | 5 | 3 | 3 | 3 | 3 | 0 | 3 | 3 | 0 |
| 87 | 1 | 0 | 1 | 1 | 3 | 0 | 0 | 0 | 0 |
| 88 | 5 | 1 | 3 | 3 | 3 | 0 | 1 | 3 | 0 |
| 88 | 1 | 1 | 1 | 2 | 3 | 0 | 1 | 3 | 0 |
| 90 | 5 | 2 | 2 | 3 | 3 | 0 | 0 | 3 | 0 |
| 90 | 1 | 1 | 2 | 3 | 3 | 0 | 0 | 2 | 0 |
| 91 | 5 | 2 | 1 | 2 | 3 | 0 | 0 | 0 | 0 |
| 91 | 1 | 1 | 0 | 1 | 3 | 0 | 0 | 0 | 0 |
| 106 | 5 | 1 | 3 | 3 | 3 | 0 | 0 | 0 | 0 |
| 106 | 1 | 0 | 1 | 3 | 3 | 0 | 0 | 0 | 0 |
| 108 | 5 | 0 | 2 | 3 | 3 | 0 | 2 | 2 | 0 |
| 108 | 1 | 0 | 1 | 2 | 2 | 0 | 1 | 2 | 0 |
| 109 | 5 | 0 | 0 | 3 | 3 | 0 | 2 | 2 | 0 |

TABLE IV-continued

POST-EMERGENCE HERBICIDAL ACTIVITY

| Compound No | APPLI-CATION Rate (kg/ha) | TEST PLANT |||||||
|---|---|---|---|---|---|---|---|---|
| | | Wh | Ot | Rg | Jm | P | Ip | Ms | Sf |
| 109 | 1 | 0 | 0 | 2 | 2 | 0 | 2 | 2 | 0 |
| 111 | 5 | 1 | 3 | 3 | 1 | 2 | 3 | 0 |
| 111 | 1 | 0 | 0 | 3 | 3 | 1 | 1 | 1 | 0 |
| 112 | 5 | 3 | 3 | 3 | 3 | 3 | 3 | 3 | 0 |
| 112 | 1 | 1 | 2 | 2 | 3 | 2 | 3 | 3 | 2 |
| 116 | 5 | 1 | 2 | 2 | 2 | 0 | 3 | 2 | 0 |
| 116 | 1 | 0 | 2 | 2 | 2 | 0 | 1 | 2 | 0 |
| 117 | 5 | 3 | 3 | 3 | 3 | 3 | 3 | 3 | 2 |
| 117 | 1 | 3 | 3 | 3 | 3 | 3 | 3 | 3 | 0 |
| 118 | 5 | 2 | 3 | 3 | 3 | 3 | 0 | 2 | 0 |
| 118 | 1 | 0 | 1 | 2 | 3 | 3 | 0 | 2 | 0 |
| 120 | 5 | 3 | 3 | 3 | 3 | 3 | 3 | 3 | 2 |
| 120 | 1 | 3 | 3 | 3 | 3 | 2 | 2 | 3 | 1 |
| 120 | 0.5 | 3 | 3 | 3 | 3 | 3 | 3 | 3 | 1 |
| 121 | 5 | 0 | 1 | 3 | 3 | 0 | 3 | 2 | 0 |
| 121 | 1 | 0 | 0 | 1 | 2 | 0 | 2 | 2 | 0 |
| 131 | 5 | 3 | 3 | 3 | 3 | 3 | 3 | 3 | 1 |
| 131 | 1 | 1 | 3 | 3 | 3 | 1 | 0 | 2 | 0 |
| 131 | 0.5 | 1 | 3 | 3 | 3 | 0 | 2 | 1 | 0 |

The names of the test plants were as follows:
Wh Wheat
Ot Wild Oats
Rg Ryegrass
Jm Japanese millet
P Peas
Ip Ipomoea
Ms Mustard
Sf Sunflower

EXAMPLE 15

The compounds were formulated for test by mixing an appropriate amount with 5 ml of an emulsion prepared by diluting 160 ml of a solution containing 21.8 g per liter of "Span" 80 and 78.2 g per liter of "Tween" 20 in methylcyclohexanone to 500 ml with water. "Span" 80 is a Trade Mark for a surface-active agent comprising sorbitan monolaurate. "Tween" 20 is a Trade Mark for a surface-active agent comprising a condensate of sorbitan monolaurate with 20 molar proportions of ethylene oxide. Each 5 ml emulsion containing a test compound was then diluted to 40 ml with water and sprayed onto young pot plants (post-emergence test) of the species named in Table V below. Damage to test plants was assessed after 14 days on a scale of 0 to 5 where 0 is 0 to 20% damage and 5 is complete kill. In a test for pre-emergence herbicidal activity, seeds of the test plants were sown in a shallow slit formed in the surface of soil in fibre trays. The surface was then levelled and sprayed, and fresh soil then spread thinly over the sprayed surface. Assessment of herbicidal damage was carried out after 21 days using the same scale of 0 to 5 as in the post-emergence test. In both cases the degree of herbicidal damage was assessed by comparison with untreated control plants. The results are given in Table V below. A dash (—) means that no experiment was carried out.

TABLE V

PART A

| Compound No | APPLICATION Method | Rate (kg/ha) | TEST PLANT |||||||||||
|---|---|---|---|---|---|---|---|---|---|---|---|---|---|
| | | | Sb | Rp | Ct | Sy | Mz | Ww | Rc | Sn | Ip | Am | Pi | Ca |
| 8 | PRE | 1 | 4 | 5 | 1 | 2 | 2 | 5 | 4 | 5 | 2 | 5 | — | 4 |
| 8 | PRE | 5 | 5 | 5 | 1 | 4 | 5 | 5 | 5 | 5 | 4 | 5 | — | 4 |
| 8 | POST | 5 | 2 | 2 | 1 | 4 | 1 | 1 | 0 | 4 | 3 | — | 3 | 2 |
| 14 | PRE | 0.5 | 5 | 4 | 0 | 1 | 4 | 5 | 2 | 0 | 2 | 5 | 5 | 4 |
| 14 | PRE | 1 | 5 | 5 | 0 | 3 | 4 | 5 | 4 | 3 | 2 | 5 | 5 | 4 |

TABLE V-continued
PART A

| Compound No | APPLICATION Method | Rate (kg/ha) | Sb | Rp | Ct | Sy | Mz | Ww | Rc | Sn | Ip | Am | Pi | Ca |
|---|---|---|---|---|---|---|---|---|---|---|---|---|---|---|
| 14 | PRE | 2.5 | 5 | 5 | 1 | 4 | 5 | 5 | 4 | 3 | 4 | 5 | 5 | 4 |
| 14 | POST | 1 | 1 | 1 | 0 | 1 | 1 | 0 | 0 | 0 | 2 | 1 | 2 | 2 |
| 14 | POST | 5 | 3 | 3 | 1 | 3 | 3 | 3 | 1 | 0 | 3 | 3 | 3 | 4 |
| 35 | PRE | 0.5 | 4 | 4 | 1 | 0 | 0 | 1 | 0 | 1 | 0 | 3 | 1 | 0 |
| 35 | PRE | 1 | 4 | 4 | 0 | 1 | 1 | 4 | 1 | 2 | 1 | 5 | 5 | 4 |
| 35 | PRE | 5 | 5 | 5 | 1 | 4 | 5 | 5 | 4 | 4 | 4 | 5 | 5 | 5 |
| 37 | PRE | 5 | 5 | 5 | 0 | 0 | 2 | 2 | 2 | 3 | 1 | 4 | 4 | 4 |
| 37 | POST | 5 | 3 | 3 | 2 | 0 | 2 | 0 | 0 | 1 | 2 | 4 | 2 | 4 |
| 38 | PRE | 1 | 5 | 5 | 0 | 0 | 0 | 1 | 0 | 3 | 0 | 5 | 3 | 4 |
| 38 | PRE | 5 | 5 | 5 | 2 | 3 | 2 | 4 | 4 | 5 | 0 | 5 | 5 | 4 |
| 38 | POST | 5 | 4 | 3 | 0 | 1 | 0 | 1 | 0 | 2 | 0 | 2 | 0 | 3 |
| 39 | PRE | 5 | 5 | 5 | 0 | 1 | 4 | 3 | 4 | 5 | 1 | 5 | 4 | 4 |
| 39 | POST | 5 | 4 | 3 | 4 | 4 | 3 | 0 | 0 | 3 | 2 | 4 | 2 | 4 |
| 44 | PRE | 2.5 | 4 | 5 | 0 | 3 | 0 | 4 | 3 | 5 | 3 | 4 | 5 | 4 |
| 44 | POST | 2.5 | 4 | 4 | 2 | 3 | 0 | 0 | 0 | 4 | 3 | 4 | 4 | 4 |
| 46 | PRE | 2.5 | 3 | 5 | 0 | 1 | 1 | 1 | 2 | 3 | 0 | 5 | 4 | 4 |
| 52 | PRE | 2.5 | 5 | 5 | 0 | 1 | 0 | 0 | 0 | 5 | 0 | 5 | 5 | 4 |
| 43 | PRE | 5 | 5 | 5 | 4 | 4 | 2 | 0 | 4 | 5 | 1 | 5 | — | 4 |
| 54 | PRE | 1 | 5 | 4 | 0 | 2 | 4 | 5 | 1 | 2 | 0 | 4 | 5 | 3 |
| 54 | PRE | 2.5 | 5 | 5 | 1 | 4 | 4 | 5 | 4 | 3 | 5 | 5 | 5 | 4 |
| 55 | PRE | 2.5 | 5 | 3 | 0 | 0 | 0 | 4 | 0 | 3 | 0 | 4 | 0 | 4 |
| 64 | PRE | 1 | 2 | 4 | 0 | 0 | 1 | 1 | 1 | 0 | 0 | 4 | — | 3 |
| 64 | PRE | 5 | 5 | 5 | 0 | 1 | 4 | 4 | 4 | 1 | 0 | 4 | — | 4 |
| 69 | PRE | 2.5 | 4 | 2 | 0 | 0 | 0 | 2 | 0 | 2 | 0 | 4 | 0 | 4 |
| 87 | POST | 2.5 | 4 | 2 | 1 | 0 | 0 | 0 | 0 | 1 | 2 | 5 | 1 | 4 |
| 88 | POST | 2.5 | 4 | 3 | 4 | 0 | 2 | 1 | 0 | 2 | 2 | 5 | 2 | 4 |
| 90 | POST | 1 | 3 | 4 | 2 | 1 | 0 | 0 | 0 | 2 | 0 | 4 | 3 | 4 |
| 90 | POST | 2.5 | 4 | 4 | 3 | 2 | 0 | 0 | 0 | 2 | 0 | 5 | 3 | 4 |

TABLE V
PART B

| Compound No | APPLICATION Method | Rate (kg/ha) | Po | Xa | Ab | Cv | Ot | Dg | Pu | St | Ec | Sh | Ag | Cn |
|---|---|---|---|---|---|---|---|---|---|---|---|---|---|---|
| 8 | PRE | 1 | 4 | 4 | 5 | — | 4 | 5 | 5 | 5 | 5 | 5 | 2 | 1 |
| 8 | PRE | 5 | 5 | 5 | 5 | — | 5 | 5 | 5 | 5 | 5 | 5 | 4 | 4 |
| 8 | POST | 5 | 4 | 4 | 3 | 3 | 1 | 4 | 4 | 2 | 3 | 1 | 0 | 1 |
| 14 | PRE | 0.5 | 5 | 1 | 5 | — | 5 | 4 | 5 | 5 | 4 | 5 | 1 | 0 |
| 14 | PRE | 1 | 5 | — | 4 | — | 5 | 4 | 5 | 5 | 5 | 4 | 4 | 2 |
| 14 | PRE | 2.5 | 5 | 0 | 5 | — | 5 | 5 | 5 | 5 | 5 | 4 | 5 | 3 |
| 14 | POST | 1 | 3 | — | 0 | — | 0 | 3 | 1 | 1 | 3 | 4 | 0 | 1 |
| 14 | POST | 5 | 4 | 2 | 3 | 3 | 3 | 4 | 3 | 4 | 4 | 4 | 1 | 3 |
| 35 | PRE | 0.5 | 4 | 3 | 0 | — | 2 | 1 | 3 | 4 | 1 | 4 | 0 | 0 |
| 35 | PRE | 1 | 5 | 3 | 3 | — | 4 | 4 | 5 | 4 | 3 | 4 | 1 | 2 |
| 35 | PRE | 5 | 5 | 3 | 5 | — | 5 | 5 | 5 | 4 | 4 | 5 | 4 | 2 |
| 37 | PRE | 5 | 5 | — | 0 | — | 2 | 4 | 4 | 5 | 3 | 5 | 0 | 0 |
| 37 | POST | 5 | 3 | 3 | 1 | 3 | 0 | 2 | 1 | 1 | 2 | 0 | 0 | 0 |
| 38 | PRE | 1 | 5 | — | 4 | — | 0 | 4 | 4 | 4 | 2 | 2 | 0 | 0 |
| 38 | PRE | 5 | 5 | — | 5 | — | 5 | 4 | 5 | 5 | 5 | 4 | 2 | 3 |
| 38 | POST | 5 | 4 | 1 | 2 | 0 | 2 | 3 | 4 | 2 | 4 | 1 | 4 | 2 |
| 39 | PRE | 5 | 5 | — | 4 | — | 4 | 5 | 5 | 5 | 5 | 5 | 4 | 3 |
| 39 | POST | 5 | 4 | 3 | 3 | 2 | 3 | 4 | 3 | 3 | 4 | 2 | 1 | 2 |
| 44 | PRE | 2.5 | 5 | — | 5 | — | 4 | 4 | 5 | 5 | 5 | 5 | 2 | 0 |
| 44 | POST | 2.5 | 4 | — | 4 | 4 | 1 | 2 | 3 | 4 | 4 | 0 | 0 | 2 |
| 46 | PRE | 2.5 | 5 | 0 | 5 | — | 4 | 4 | 4 | 4 | 4 | 5 | 4 | 1 | 0 |
| 52 | PRE | 2.5 | 5 | — | 5 | — | 5 | 3 | 5 | 5 | 5 | 2 | 0 | 0 |
| 43 | PRE | 5 | 5 | 1 | 4 | — | 0 | 4 | 4 | 5 | 4 | 2 | 0 | 2 |
| 54 | PRE | 1 | 5 | 0 | 2 | 4 | 4 | 4 | 4 | 4 | 4 | 1 | 3 | 2 |
| 54 | PRE | 2.5 | 5 | 0 | 5 | — | 5 | 4 | 5 | 5 | 5 | 3 | 4 | 4 |
| 55 | PRE | 2.5 | 5 | 0 | 4 | — | 4 | 4 | 4 | 4 | 5 | 4 | 3 | 0 |
| 64 | PRE | 1 | 3 | 0 | 4 | — | 2 | 3 | 4 | 5 | 3 | 0 | 0 | 0 |
| 64 | PRE | 5 | 5 | 0 | 5 | — | 4 | 4 | 4 | 4 | 4 | 4 | 5 | 1 |
| 69 | PRE | 2.5 | 5 | 0 | 5 | — | 4 | 2 | 3 | 4 | 5 | 4 | 3 | 1 |
| 87 | POST | 2.5 | 5 | 1 | 3 | 4 | 0 | 1 | 2 | 2 | 1 | 0 | 1 | 0 |
| 88 | POST | 2.5 | 5 | 1 | 2 | 4 | 0 | 2 | 2 | 0 | 0 | 0 | 0 | 0 |
| 90 | POST | 1 | 5 | 1 | 4 | 4 | 0 | 1 | 2 | 2 | 1 | 0 | 0 | 0 |

TABLE V-continued

PART B

| Compound No | APPLICATION Method Rate (kg/ha) | TEST PLANT | | | | | | | | | | |
|---|---|---|---|---|---|---|---|---|---|---|---|---|
| | | Po | Xa | Ab | Cv | Ot | Dg | Pu | St | Ec | Sh | Ag | Cn |
| 90 | POST 2.5 | 5 | 2 | 2 | 4 | 0 | 2 | 2 | 0 | 0 | 0 | 0 | 0 |

The names of the test plants were as follows:
Sb Sugar beet
Rp Rape
Ct Cotton
Sy Soya bean
Mz Maize
Ww Winter wheat
Rc Rice
Sn *Senecio vulgaris*
Ip *Ipomoea purpurea*
Am *Amaranthus retroflexus*
Pi *Polygonum aviculare*
Ca *Chenopodium album*
Po *Portulaca oleracea*
Xa *Xanthium pensylvanicum*
Ab *Abutilon theophrastii*
Cv *Convolvulus arvensis*
Ot Cultivated oats and wild oats (*Avena fatua*) Wild oats are used in the post-emergence test and cultivated oats in the pre-emergence test
Dg *Digitaria sanguinalis*
Pu *Poa annua*
St *Setaria viridis*
Ec *Echinochloa crus-galli*
Sh *Sorghum halepense*
Ag *Agropyron repens*
Cn *Cyperus rotundus*

EXAMPLE 16

This Example demonstrates the selective herbicidal activity of certain compounds used in the process of the invention as pre-emergent herbicides.

The procedure described in Example 13 was repeated using as the test species wheat and annual rye grass. The effect of the pre-emergence treatment was assessed visually after 29 days and the results are presented in Table VI where the damage to the plants is rated on a scale from 0 to 10 where 0 represents no damage to the plant and 10 represents complete kill.

TABLE VI

| COMPOUND NO | APPLICATION RATE (kg/ha) | TEST PLANT | |
|---|---|---|---|
| | | Wheat | Annual Rye Grass |
| 3 | 2 | 0 | 10 |
| 3 | 1 | 0 | 6 |
| 3 | 0.5 | 0 | 1 |
| 3 | 0.1 | 0 | 0 |

The procedure described in Example 13 was repeated using as the test species wheat, annual rye grass and Japanese millet. The effect of the pre-emergence treatment was assessed visually after 29 days and the results are presented in Table VII where the damage to the plants is rated on a scale from 0 to 3 where 0 represents no damage to the plant and 3 represents complete kill.

TABLE VII

| COMPOUND NO | APPLICATION RATE (kg/ha) | TEST PLANT | | |
|---|---|---|---|---|
| | | Wheat | Rye Grass | Japanese Millet |
| 47 | 5 | 0 | 3 | 3 |
| 47 | 1 | 0 | 3 | 3 |

EXAMPLE 17

This Example illustrates the selective herbicidal activity of compound no 22 when applied pre-emergence in the field.

The test compound (22) was formulated following essentially the same procedure as that described in Example 14.

The seeds of the test plant species were sown on flat topped hills spaced 1 meter apart using a Stanhay Precision Seeder, two plant species being sown on each hill. The plots were pegged to 1.25 meter centres and two days after showing they were sprayed to a width of 1 meter with the appropriate concentration formulated test-compound using an Oxford Precision Sprayer fitted with two No "0" T-jets and having an output of 250 l/hr. The site was sprinkler irrigated throughout the duration of the trial.

Each test had two replicates and damage was assessed 42 days after spraying by visual scoring on a percentage scale wherein 0% represents no damage and 100% represents complete kill. The results are given in Table VIII below.

TABLE VIII

| APPLICATION RATE (kg/ha) | TEST PLANTS | | | | | | | | |
|---|---|---|---|---|---|---|---|---|---|
| | CROPS | | | | | WEEDS | | | |
| | Mz | Sg | Sr | Ct | Sy | Ip | Am | Po | Ec |
| 0 | 5 | 0 | 0 | 0 | 10 | 0 | 0 | 10 | 20 |
| 1 | 0 | 0 | 0 | 0 | 5 | 5 | 25 | 10 | 20 |
| 2 | 0 | 0 | 0 | 0 | 0 | 0 | 83 | 90 | 40 |
| 4 | 0 | 0 | 0 | 0 | 5 | 75 | 85 | 100 | 55 |

The names of the test plants are as follows:

| Code | Species | Variety |
|---|---|---|
| Mz | Maize | XL 361 |
| Sg | Sorghum | NK 207 |
| Sr | Sunflower | sunfola |
| Ct | Cotton | Delta Pine |
| Sy | Soyabean | Clark 63 |
| Ip | *Ipomoea* | |
| Am | *Amaranthus* | *retroflexus* |
| Po | *Portulaca* | *oleracea* |
| Ec | *Echinochloa* | *crus-gaili**|

*Volunteer species (not sown)

EXAMPLE 18

This Example is a comparative Example not of the invention and demonstrates the efficacy of the compounds of the invention in comparison to preferred compounds specifically disclosed by Jojima and Tamura in Japanese Patent No. 9474/67 and in Agricultural and Biological Chemistry, Vol. 30, No. 9, pp 896–905, 1966.

(a) A number of 2-phenoxypyrimidines and 4-phenoxypyrimidines, outside the scope of the present invention but specifically mentioned in the references cited above, were prepared in order to compare their herbicidal activity with the activity of the compounds of the invention. The compounds are tabulated below.

2-PHENOXYPYRIMIDINES

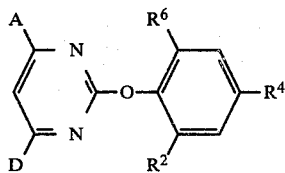

| COMPOUND NO | SUBSTITUENTS | | | | |
|---|---|---|---|---|---|
| | A | D | $R^2$ | $R^4$ | $R^6$ |
| 201 | H | H | H | H | H |
| 202 | H | H | Cl | Cl | H |
| 203 | CH$_3$ | CH$_3$ | H | H | H |
| 204 | H | H | CH$_3$O | H | H |
| 205 | CH$_3$ | CH$_3$ | CH$_3$O | H | H |

4-PHENOXYPYRIMIDINES

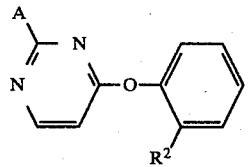

| COMPOUND NO | SUBSTITUENTS | |
|---|---|---|
| | A | $R^2$ |
| 206 | Cl | H |
| 207 | Cl | CH$_3$O |

The compounds 201 to 207 above were formulated according to the process described in Example 12 and their pre-emergent and post-emergent herbicidal activity was assessed following the procedure described in Examples 13 and 14 respectively. The results are presented below:

| COMPOUND NO+ | APPLICATION Method Rate (kg/ha) | | TEST PLANT | | | | | | |
|---|---|---|---|---|---|---|---|---|---|
| | | | Wh | Ot | Rg | Jm | P | Ip | Ms | Sf |
| 201 | PRE | 5 | 0 | 0 | 0 | 0 | 0 | 0 | 0 | 0 |
| 201 | POST | 5 | 0 | 0 | 0 | 0 | 0 | 0 | 0 | 0 |
| 202 | PRE | 5 | 0 | 0 | 0 | 0 | 0 | 0 | 0 | 0 |
| 202 | POST | 5 | 0 | 0 | 0 | 0 | 0 | 0 | 0 | 0 |
| 203 | PRE | 5 | 0 | 0 | 0 | 0 | 0 | 0 | 0 | 0 |
| 203 | POST | 5 | 0 | 0 | 0 | 0 | 0 | 0 | 0 | 0 |
| 204 | PRE | 5 | 0 | 0 | 0 | 0 | 0 | 0 | 0 | 0 |
| 204 | POST | 5 | 0 | 0 | 0 | 0 | 0 | 0 | 0 | 0 |
| 205 | PRE | 5 | 0 | 0 | 0 | 0 | 0 | 0 | 0 | 0 |
| 205 | POST | 5 | 0 | 0 | 0 | 0 | 0 | 0 | 3 | 0 |
| 206 | PRE | 5 | 0 | 0 | 0 | 0 | 0 | 0 | 0 | 0 |
| 206 | POST | 5 | 0 | 0 | 0 | 0 | 0 | 0 | 0 | 0 |
| 207 | PRE | 5 | 0 | 0 | 0 | 0 | 0 | 0 | 0 | 0 |
| 207 | POST | 5 | 0 | 0 | 0 | 0 | 0 | 0 | 0 | 0 |

+Twenty-five 4-phenoxypyrimidines bearing a wide range of substituents were prepared and tested by the applicants. A few of these compounds showed very weak activity at an application rate of 5 kg/ha and none showed activity at an application rate of 1 kg/ha.

(b) The significantly and unexpectedly higher herbicidal activity of 2-phenoxypyrimidines having the substitution pattern of the compounds of the present invention is perhaps best illustrated by direct comparison of the herbicidal activity of compounds not having the substitution pattern of the compounds of the invention and analogous compounds of the invention. The results of such comparisons are presented below wherein the compounds were formulated according to the process described in Example 12 and their pre-emergent and post-emergent herbicidal activity was assessed following the procedure described in Examples 13 and 14 respectively.

(i)

[Structures of compounds 204 and 205]

204 and 205

| COMPOUND NO | APPLICATION Method Rate (kg/ha) | | TEST PLANT | | | | | | | |
|---|---|---|---|---|---|---|---|---|---|---|
| | | | Wh | Ot | Rg | Jm | P | IP | Ms | Sf |
| 204 | PRE | 5 | 0 | 0 | 0 | 0 | 0 | 0 | 0 | 0 |
| 204 | POST | 5 | 0 | 0 | 0 | 0 | 0 | 0 | 0 | 0 |
| 205 | PRE | 5 | 0 | 0 | 0 | 0 | 0 | 0 | 0 | 0 |
| 205 | POST | 5 | 0 | 0 | 0 | 0 | 0 | 0 | 3 | 0 | and for comparison

[Structure of compound 4]

4

[Structure of compound 8]

8

| COMPOUND NO | APPLICATION Method Rate (kg/ha) | | TEST PLANT | | | | | | | |
|---|---|---|---|---|---|---|---|---|---|---|
| | | | Wh | Ot | Rg | Jm | P | Ip | Ms | Sf |
| 4 | PRE | 5 | 1 | 0 | 0 | 1 | 3 | 3 | 3 | 2 |
| 4 | POST | 5 | 0 | 0 | 0 | 3 | 0 | 3 | 0 | 0 |
| 4 | PRE | 1 | 0 | 0 | 0 | 0 | 3 | 3 | 1 | 0 |
| 4 | POST | 1 | 0 | 0 | 0 | 0 | 0 | 0 | 0 | 0 |
| 8 | PRE | 5 | 3 | 3 | 3 | 3 | 3 | 3 | 3 | 3 |
| 8 | POST | 5 | 3 | 3 | 3 | 3 | 3 | 3 | 3 | 3 |
| 8 | PRE | 1 | 1 | 3 | 3 | 3 | 2 | — | 3 | — |
| 8 | POST | 1 | 3 | 3 | 3 | 3 | 2 | 3 | 2 | — |

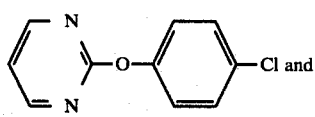 (ii)

211+

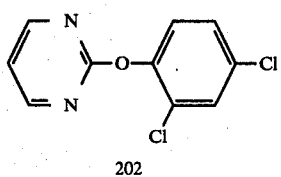

202

| COM-<br>POUND<br>NO | APPLICATION | | TEST PLANT | | | | | | | |
|---|---|---|---|---|---|---|---|---|---|---|
| | Method | Rate<br>(kg/ha) | Wh | Ot | Rg | Jm | P | Ip | Ms | Sf |
| 211 | PRE | 5 | 0 | 0 | 0 | 2 | 0 | 0 | 0 | 0 |
| 211 | POST | 5 | 0 | 0 | 0 | 0 | 0 | 0 | 0 | 0 |
| 202 | PRE | 5 | 0 | 0 | 0 | 0 | 0 | 0 | 0 | 0 |
| 202 | POST | 5 | 0 | 0 | 0 | 0 | 0 | 0 | 0 | 0 |

+A compound not of this invention and not specifically disclosed in the above cited references but useful in demonstrating the effect of substitution pattern in the herbicidal activity of 2-phenoxypyrimidines.

and for comparison

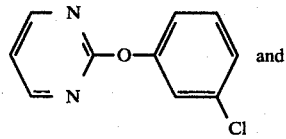 and

5

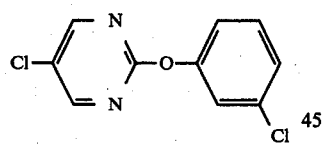

8

| COM-<br>POUND<br>NO | APPLICATION | | TEST PLANT | | | | | | | |
|---|---|---|---|---|---|---|---|---|---|---|
| | Method | Rate<br>(kg/ha) | Wh | Ot | Rg | Jm | P | Ip | Ms | Sf |
| 5 | PRE | 5 | 1 | 2 | 2 | 3 | 2 | 3 | 3 | 1 |
| 5 | POST | 5 | 1 | 2 | 3 | 3 | 1 | 3 | 2 | — |
| 5 | PRE | 1 | 0 | 0 | 0 | 0 | 0 | 0 | 0 | 0 |
| 5 | POST | 1 | 0 | 0 | 0 | 2 | 0 | 0 | 0 | — |
| 8 | PRE | 5 | 3 | 3 | 3 | 3 | 3 | 3 | 3 | 3 |
| 8 | POST | 5 | 3 | 3 | 3 | 3 | 3 | 3 | 3 | 3 |
| 8 | PRE | 1 | 1 | 3 | 3 | 3 | 2 | — | 3 | — |
| 8 | POST | 1 | 3 | 3 | 3 | 3 | 2 | 3 | 2 | — |

We claim:

1. A process of inhibiting the growth of, severely damaging, or killing plants which process comprises applying to the plant or to the growth medium thereof an effective amount of a composition comprising as active ingredient a compound of formula I:

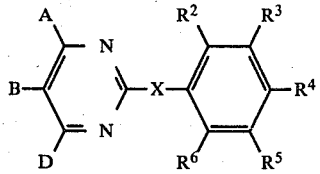

wherein A and D are independently chosen from the group consisting of hydrogen, halogen, $C_1$ to $C_6$ alkyl, $C_1$ to $C_6$ haloalkyl, $C_1$ to $C_6$ alkoxy, $C_1$ to $C_6$ alkylthio, $C_1$ to $C_6$(alkoxy)carbonyl and $NR^7R^8$ wherein $R^7$ and $R^8$ are independently chosen from hydrogen and $C_1$ to $C_6$ alkyl;

B is chosen from the group consisting of halogen, cyano, $C_1$ to $C_6$(alkoxy)carbonyl, $C_1$ to $C_6$ alkyl, $C_1$ to $C_6$ haloalkyl, $C_1$ to $C_6$ alkoxy, $NR^7R^8$ wherein $R^7$ and $R^8$ are independently hydrogen or $C_1$ to $C_6$ alkyl, phenyl, halophenyl and nitrophenyl;

$R^3$ and $R^5$ are independently chosen from the group consisting of hydrogen, halogen, nitro, cyano, $C_1$ to $C_6$ alkyl, $C_2$ to $C_6$ alkenyl, $C_1$ to $C_6$ haloalkyl, $C_1$ to $C_6$ alkoxy, $C_1$ to $C_6$ haloalkoxy, $C_2$ to $C_6$ alkenyloxy, $C_2$ to $C_6$ haloalkenyloxy, $C_2$ to $C_6$ alkynyloxy, phenoxy, halophenoxy, benzyloxy and halobenzyloxy, and wherein at least one of $R^3$ and $R^5$ is a substituent other than hydrogen;

$R^2$, $R^4$ and $R^6$ are independently chosen from the group consisting of hydrogen, halogen, nitro, cyano, hydroxy, $C_1$ to $C_6$ alkyl, $C_2$ to $C_6$ alkenyl, $C_1$ to $C_6$ haloalkyl, $C_1$ to $C_6$ alkoxy, benzyl, phenoxy, halophenoxy, benzyloxy and halobenzyloxy;

X is oxygen;

or an acid addition salt thereof; and a carrier therefor.

2. A process according to claim 1 wherein in the compound of formula I:

A and D are both hydrogen;

B is selected from the group consisting of fluorine, chlorine, bromine, iodine and methyl; at least one of $R^3$ and $R^5$ is chosen from the group consisting of fluorine, chlorine, bromine, iodine, methyl, ethyl, isopropyl, tertiary butyl, trifluoromethyl, methoxy, ethoxy, propoxy, 3-chloropropoxy, 1,1,2,2-tetrafluoroethoxy, allyloxy, 2-chloroallyloxy, 2-propynyloxy, 4-chlorophenoxy, 4-fluorophenoxy, 4-fluorobenzyloxy, 4-chlorobenzyloxy and benzyloxy; and the remaining $R^2$ to $R^6$ substituents are chosen from hydrogen, chlorine and methyl.

3. A process according to claim 1 wherein in the compound of formula I:

A, D, $R^2$, $R^4$, $R^5$ and $R^6$ are all hydrogen;

B is selected from the group consisting of fluorine, chlorine, bromine and iodine; and $R^3$ is selected from the group consisting of chlorine, bromine, iodine and trifluoromethyl.

4. A process according to claim 1 wherein in the compound of formula I:

A, D, $R^2$, $R^4$, $R^5$ and $R^6$ are all hydrogen;

B is methyl; and $R^3$ is selected from the group consisting of chlorine, bromine, iodine and trifluoromethyl.

5. A process according to claim 1 wherein in the compound of formula I:

A, D, $R^2$, $R^4$, $R^5$ and $R^6$ are all hydrogen;

B is selected from the group consisting of fluorine, chlorine, bromine and iodine; and $R^3$ is selected from the group consisting of 3-chloropropoxy, 1,1,2,2-tetrafluoroethoxy, allyloxy, 2-chloroallyloxy, 2-propynyloxy, 4-chlorophenoxy, 4-fluorophenoxy, benzyloxy, 4-fluorobenzyloxy and 4-chlorobenzyloxy.

6. A process according to claim 1 wherein the compound has the formula

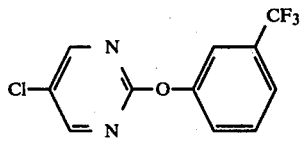

7. A process according to claim 1 wherein the compound has the formula

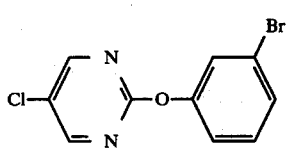

8. A process according to claim 1 wherein the compound has the formula

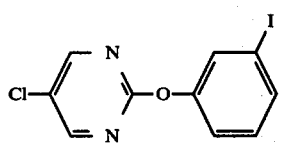

9. A process according to claim 1 wherein the compound has the formula

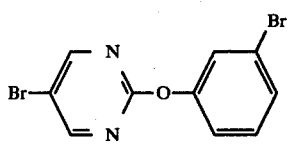

10. A process according to claim 1 wherein the compound has the formula

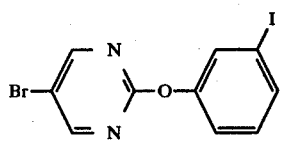

11. A process according to claim 1 wherein the compound has the formula

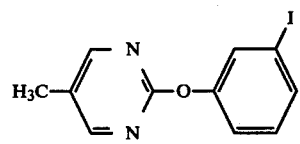

12. A process according to claim 1 wherein the compound has the formula

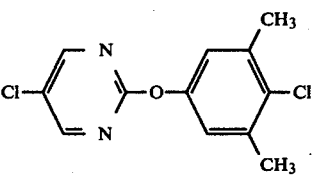

13. A process according to claim 1 wherein the compound has the formula

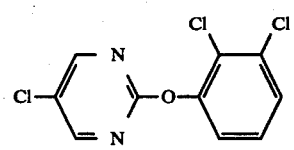

14. A process according to claim 1 wherein the compound has the formula

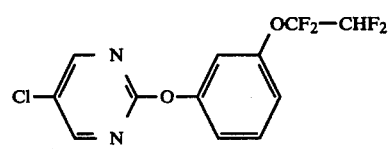

15. A process according to claim 1 wherein the compound has the formula

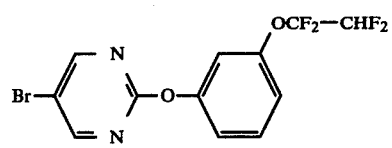

16. A process according to claim 1 wherein the compound has the formula

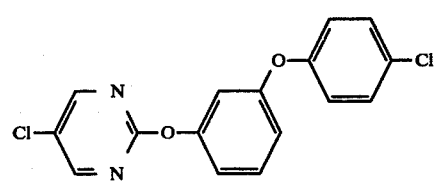

17. A process according to claim 1 wherein the compound has the formula

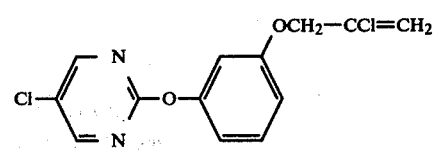

18. A process according to claim 1 wherein the compound has the formula

19. A process according to claim 1 wherein the compound has the formula

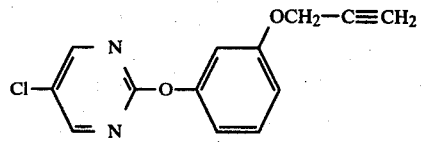

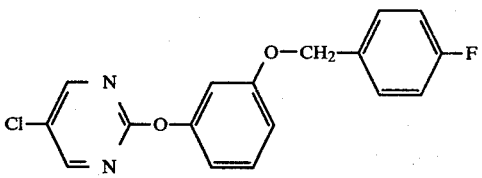

20. A process according to claim 1 for selectively controlling the growth of weeds in crops.

21. A process according to claim 20 wherein the crops are cotton crops or sunflower crops.

22. A process according to claim 20 wherein the crops are cereal crops.

23. A process according to claim 1 wherein the compound of formula I is applied at a rate in the range from 0.01 to 10 kilograms per hectare.

24. A process according to claim 23 wherein the rate is in the range from 0.1 to 5 kilograms per hectare.

* * * * *